(12) United States Patent
Schramm et al.

(10) Patent No.: US 8,916,571 B2
(45) Date of Patent: Dec. 23, 2014

(54) METHODS OF TREATING CANCER USING INHIBITORS OF 5'-METHYLTHIOADENOSINE PHOSPHORYLASE

(75) Inventors: Vern L. Schramm, New Rochelle, NY (US); Chandan Guha, Scarsdale, NY (US)

(73) Assignee: Albert Einstein College of Medicine of Yeshiva University, Bronx, NY (US)

(*) Notice: Subject to any disclaimer, the term of this patent is extended or adjusted under 35 U.S.C. 154(b) by 1886 days.

(21) Appl. No.: 12/224,073

(22) PCT Filed: Feb. 23, 2007

(86) PCT No.: PCT/NZ2007/000036
§ 371 (c)(1),
(2), (4) Date: Apr. 5, 2010

(87) PCT Pub. No.: WO2007/097647
PCT Pub. Date: Aug. 30, 2007

(65) Prior Publication Data
US 2010/0222370 A1 Sep. 2, 2010

Related U.S. Application Data

(60) Provisional application No. 60/776,411, filed on Feb. 24, 2006.

(51) Int. Cl.
*A61K 31/519* (2006.01)
*C07D 487/04* (2006.01)
*A61P 35/00* (2006.01)
*A61K 31/7042* (2006.01)

(52) U.S. Cl.
CPC ............ *A61K 31/519* (2013.01); *A61K 31/7042* (2013.01)
USPC ........ 514/265.1; 514/300; 544/280; 546/113; 546/116

(58) Field of Classification Search
CPC ............................ A61K 31/519; C07D 487/04
USPC .......... 514/265.1, 300; 544/280; 546/113, 118
See application file for complete search history.

(56) References Cited

U.S. PATENT DOCUMENTS

| | | | |
|---|---|---|---|
| 5,985,848 A | 11/1999 | Furneaux et al. |
| 6,066,722 A | 5/2000 | Furneaux et al. |
| 6,228,847 B1 | 5/2001 | Furneaux et al. |
| 6,458,799 B1 | 10/2002 | Montgomery et al. |
| 6,492,347 B2 | 12/2002 | Furneaux et al. |
| 6,693,193 B1 | 2/2004 | Furneaux et al. |
| 6,803,455 B2 | 10/2004 | Furneaux et al. |
| 7,022,852 B2 | 4/2006 | Furneaux et al. |
| 7,098,334 B2 | 8/2006 | Furneaux et al. |
| 7,109,331 B2 | 9/2006 | Furneaux et al. |
| 7,211,653 B2 | 5/2007 | Furneaux et al. |
| 7,211,677 B2 | 5/2007 | Furneaux et al. |
| 7,390,890 B2 | 6/2008 | Furneaux et al. |
| 7,405,297 B2 | 7/2008 | Furneaux et al. |
| 7,553,839 B2 | 6/2009 | Evans et al. |
| 7,655,795 B2 | 2/2010 | Evans et al. |
| 8,173,662 B2 | 5/2012 | Evans et al. |
| 2006/0160765 A1 | 7/2006 | Evans et al. |
| 2006/0217551 A1 | 9/2006 | Evans et al. |
| 2007/0015772 A1 | 1/2007 | Furneaux et al. |
| 2008/0280334 A1 | 11/2008 | Lenz et al. |
| 2009/0012104 A1 | 1/2009 | Babu et al. |
| 2009/0233948 A1 | 9/2009 | Evans et al. |
| 2009/0239885 A1 | 9/2009 | Evans et al. |
| 2009/0325986 A1 | 12/2009 | Furneaux et al. |
| 2010/0062995 A1 | 3/2010 | Schramm |
| 2010/0094003 A1 | 4/2010 | Evans et al. |
| 2010/0168141 A1 | 7/2010 | Evans et al. |

FOREIGN PATENT DOCUMENTS

| | | |
|---|---|---|
| WO | WO 03/080620 A1 | 10/2003 |
| WO | WO 2004/018496 | 3/2004 |
| WO | WO 2005/118532 | 12/2005 |
| WO | 2006014913 A2 | 2/2006 |
| WO | WO 2006/014913 A2 | 2/2006 |
| WO | WO 2006/123953 | 11/2006 |
| WO | WO 2007/016291 | 2/2007 |
| WO | WO 2007/069923 | 6/2007 |
| WO | WO 2007/097643 A1 | 8/2007 |
| WO | WO 2007/097648 A1 | 8/2007 |
| WO | WO 2008/030118 | 3/2008 |
| WO | WO 2008/030119 | 3/2008 |
| WO | WO 2008/039324 | 4/2008 |
| WO | WO 2008/079028 | 7/2008 |
| WO | 2010033236 A2 | 3/2010 |

OTHER PUBLICATIONS

Communication Supplementary European Search Report received from the European Patent Office dated Nov. 17, 2010 in connection with European Patent Application No. 07715988.7, 7 pages.
Basu I et al, entitled "Growth and Metastases of Human Lung Cancer Are Inhibited in Mouse Xenografts by a Transition State Analogue of 5'-Methlthioadenosine Phosphorylase," The Journal of Biological Chemistry, vol. 286, No. 6, 4902-4911, Feb. 11, 2011.
Gutierrez J A et al., entitled "Transition state analogs of 5'-methylthioadenosine nucleosidase disrupt quorum sensing," Nature Chemical Biology, vol. 5, No. 4, Apr. 2009, 251-257.
Evans G B et al., entitled "Second Generation Transition State Analogue Inhibitors of Human 5'-5'- Methylthioadenosine Phosphorylase," J. Med. Chem, 2005, 48, 4679-4689.
Evans G B et al., entitled "Targeting the Polyamine Pathway with Transition-State Analogue Inhibitors of 5'- Methylthioadenosine Phosphorylase," J. Med. Chem., 2004, 47, 3275-3281.
Basu I et al., entitled "A Transition State Analogue of 5'-Methylthioadenosine Phosphorylase Induces Apoptosis in Head and Neck Cancers," The Journal of Biologoca; Chemistry, vol. 282, No. 29, 21477-21486, Jul. 20, 2007.

(Continued)

*Primary Examiner* — Sreeni Padmanabhan
*Assistant Examiner* — Sahar Javanmard
(74) *Attorney, Agent, or Firm* — Amster, Rothstein & Ebenstein LLP

(57) ABSTRACT

The invention relates to the treatment of cancer using an inhibitor of 5'-methylthioadenosine phosphorylase (MTAP). The invention particularly relates to the treatment of prostate cancer and head and neck cancer.

16 Claims, 27 Drawing Sheets

(56) References Cited

OTHER PUBLICATIONS

Yamanaka H et al., entitled "Synergistic Inhibition of Polyamine Synthesis and Growth by Difluromethylornithine plus Methylthioadenosine in Methylthioadenosine Phosphorylase-deficient Murine Lymphoma Cells," Cancer Research, 47, 1771-1774, Apr. 1, 1987.

Singh V et al., entitled "Femtomolar Transition State Analogue Inhibitors of 5'-Methylthioadenosine/S-Adenosylhomocysteine Nucleosidase from *Escherichia coli*," The Journal of Biological Chemistry, vol. 280, No. 18, Issue of May 6, 18265-18273, 2005.

Communication European Search Report received by the European Patent Office dated Nov. 17, 2010 in connection with European Patent Application No. 07715988.7, 7 pages.

Basu I et al., entitled "MT-DADMe-ImmA: A novel MTAP inhibitor with potential for the treatment of human and neck prostate carcinoma," Proc Amer Assoc Cancer Res, vol. 26, 2005, 3 pages (Abstract and poster).

Polanski G et al., entitled "Transition state analogues inhibitors of Methylthioadenosine Phosphorylase (MTAP), polyamine biosynthesis, and prostate cancer," Proc Amer Assoc Cancer Res., vol. 46, 2005, 3 pages (Abstract and poster).

Basu I et al., entitled Methylthioadenosine phosphorylase inhibition and methylthioadenosine accumulation are cytotoxic to human head and neck squamous cell carcinoma cells, Proc Amer Assoc Cancer Res, vol. 47, 2006, 2 pages (Abstract).

Basu I et al., entitled Abstract #1810: A pico-molar 5'-methylthioadenosine phosphorylase transition state analog inhibits human lung cancer growth and metastases in mouse xenografts, 100th AACR Annual Meeting, Apr. 18-22, 2009, 2 pages (Abstract).

METHODS OF TREATING CANCER USING INHIBITORS OF 5'-METHYLTHIOADENOSINE PHOSPHORYLASE

CROSS-REFERENCE TO RELATED APPLICATIONS

This application is a U.S. national stage entry under 35 U.S.C. §371 of PCT International Patent Application No. PCT/NZ2007/000036, filed Feb. 23, 2007, and claims priority to U.S. Provisional Patent Application No. 60/776,411, filed Feb. 24, 2006, the contents of which are incorporated herein by reference in their entirety.

STATEMENT OF GOVERNMENT SUPPORT

This invention was made with government support under Grant No. GM41916 awarded by the National Institutes of Health. The government has certain rights in the invention.

TECHNICAL FIELD

The present invention relates to methods of treating cancer by administering to a patient in need thereof one or more inhibitors of 5'-methylthioadenosine phosphorylase (MTAP). In particular, the invention relates to methods of treating prostate cancer or head and neck cancer.

BACKGROUND

Certain nucleoside analogues have been identified as potent inhibitors of 5'-methylthioadenosine phosphorylase (MTAP) and 5'-methylthioadenosine nucleosidase (MTAN). These are the subject of U.S. Pat. No. 7,098,334.

Compounds where the location of the nitrogen atom in the sugar ring is varied or where two nitrogen atoms form part of the sugar ring, have also been identified as inhibitors of MTAP and MTAN. These compounds are described in U.S. Ser. No. 10/524,995.

MTAP and MTAN function in the polyamine biosynthesis pathway, in purine salvage in mammals, and in the quorum sensing pathways in bacteria. MTAP catalyses the reversible phosphorolysis of methylthioadenosine (MTA) to adenine and 5-methylthio-α-D-ribose-1-phosphate (MTR-1P). MTAN catalyses the reversible hydrolysis of MTA to adenine and 5-methylthio-α-D-ribose and of S-adenosyl-L-homocysteine (SAH) to adenine and S-ribosyl-homocysteine (SRH). The adenine formed is subsequently recycled and converted into nucleotides. Essentially, the only source of free adenine in the human cell is a result of the action of these enzymes. The MTR-1P is subsequently converted into methionine by successive enzymatic actions.

MTA is a by-product of the reaction involving the transfer of an aminopropyl group from decarboxylated S-adenosyl-methionine to putrescine during the formation of spermidine. The reaction is catalyzed by spermidine synthase. Likewise, spermine synthase catalyses the conversion of spermidine to spermine, with concomitant production of MTA as a by-product. The spermidine synthase is very sensitive to product inhibition by accumulation of MTA. Therefore, inhibition of MTAP or MTAN severely limits the polyamine biosynthesis and the salvage pathway for adenine in the cells.

Although MTAP is abundantly expressed in normal cells and tissues, MTAP deficiency due to a genetic deletion has been reported with many malignancies. The loss of MTAP enzyme function in these cells is known to be due to homozygous deletions on chromosome 9 of the closely linked MTAP and p16/MTS1 tumour suppressor gene. As absence of p16/MTS1 is probably responsible for the tumour, the lack of MTAP activity is a consequence of the genetic deletion and is not causative for the cancer. However, the absence of MTAP alters the purine metabolism in these cells so that they are mainly dependent on the de novo pathway for their supply of purines.

MTA has been shown to induce apoptosis in dividing cancer cells, but to have the opposite, anti-apoptotic effect on dividing normal cells such as hepatocytes (E. Ansorena et al., Hepatology, 2002, 35: 274-280).

MTAP inhibitors may therefore be used in the treatment of cancer. Such treatments are described in U.S. Pat. No. 7,098,334 and U.S. Ser. No. 10/524,995.

The need for new cancer therapies remains ongoing. For some prevalent cancers the treatment options are still limited. Prostate cancer, for example, is the most commonly diagnosed non-skin cancer in the United States. Current treatment options include radical prostatectomy, radiation therapy, hormonal therapy, and watchful waiting. Although the therapies may offer successful treatment of an individual's condition, the pitfalls are quite unfavorable and lead to a decrease in a man's overall quality of life. Surgery may inevitably result in impotence, sterility, and urinary incontinence. Side effects associated with radiation therapy include damage to the bladder and rectum as well as slow-onset impotence. Hormonal therapy will not cure the cancer and eventually most cancers develop a resistant to this type of therapy. The major risk associated with watchful waiting is that it may result in tumour growth, cancer progression and metastasis. It is therefore desirable that a better treatment option is made available to patients diagnosed with prostate cancer.

It is an object of the invention to provide a method of treating cancer, particularly prostate or head and neck cancer, or at least to provide a useful choice.

STATEMENTS OF INVENTION

In a first aspect, the invention provides a method of treating cancer comprising administering to a patient in need thereof a compound of the formula (I):

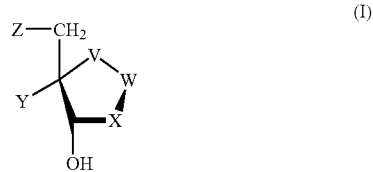

wherein:
V is selected from $CH_2$ and NH, and W is selected from $CHR^1$, $NR^1$ and $NR^2$; or V is selected from $NR^1$ and $NR^2$, and W is selected from $CH_2$ and NH;
X is selected from $CH_2$ and CHOH in the R or S-configuration;
Y is selected from hydrogen, halogen and hydroxy, except where V is selected from NH, $NR^1$ and $NR^2$ then Y is hydrogen;
Z is selected from hydrogen, halogen, hydroxy, SQ, OQ and Q, where Q is alkyl, aralkyl or aryl, each of which is optionally substituted with one or more substituents selected from hydroxy, halogen, methoxy, amino, or carboxy;

$R^1$ is a radical of the formula (II)

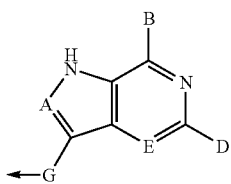
(II)

$R^2$ is a radical of the formula (III)

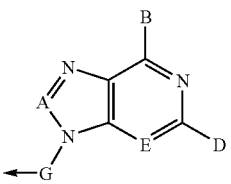
(III)

A is selected from N, CH and $CR^3$, where $R^3$ is alkyl, aralkyl or aryl, each of which is optionally substituted with one or more substituents selected from hydroxy and halogen; or $R^3$ is hydroxyl, halogen, $NH_2$, $NHR^4$, $NR^4R^5$; or $SR^6$, where $R^4$, $R^5$ and $R^6$ are alkyl, aralkyl or aryl groups, each of which is optionally substituted with one or more substituents selected from hydroxy and halogen;

B is selected from $NH_2$ and $NHR^7$, where $R^7$ is alkyl, aralkyl or aryl, each of which is optionally substituted with one or more substituents selected from hydroxy and halogen;

D is selected from hydroxy, $NH_2$, $NHR^8$, hydrogen, halogen and $SCH_3$, where $R^8$ is alkyl, aralkyl or aryl, each of which is optionally substituted with one or more substituents selected from hydroxy and halogen;

E is selected from N and CH;

G is selected from $CH_2$ and NH, or G is absent, provided that where W is $NR^1$ or $NR^2$ and G is NH then V is $CH_2$, and provided that where V is $NR^1$ or $NR^2$ and G is NH then W is $CH_2$; and provided that where W is $CHR^1$ then G is absent and V is NH;

or a tautomer thereof, or a pharmaceutically acceptable salt thereof, or a prodrug thereof.

Preferably the compound of formula (I) excludes (3R,4S)-1-[(9-deazaadenin-9-yl)methyl]-3-hydroxy-4-(methylthiomethyl)pyrrolidine.

In preferred embodiments of the invention Z is SQ. In some embodiments Z is not methylthio.

Preferably Q is an alkyl group, optionally substituted with one or more substituents selected from hydroxy, halogen, methoxy, amino, and carboxy. It is further preferred that the alkyl group is a $C_1$-$C_6$ alkyl group, most preferably a methyl group.

It is also preferred that Q is an aryl group, optionally substituted with one or more substituents selected from hydroxy, halogen, methoxy, amino, and carboxy. More preferably the aryl group is a phenyl or benzyl group.

Preferably G is $CH_2$. It is also preferred that V is $CH_2$ and W is $NR^1$. It is further preferred that B is $NH_2$. It is also preferred that D is H, and it is preferred that A is CH.

Preferably any halogen is chlorine or fluorine.

In preferred embodiments of the invention the compound of formula (I) is a compound of the formula (IV):

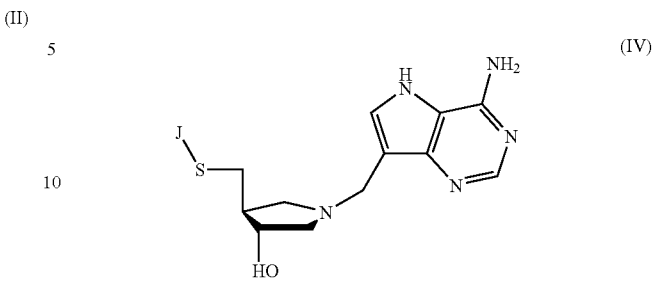
(IV)

where J is aryl, aralkyl or alkyl, each of which is optionally substituted with one or more substituents selected from hydroxy, halogen, methoxy, amino, and carboxy.

Preferably J is $C_1$-$C_7$ alkyl. More preferably J is methyl, ethyl, n-propyl, i-propyl, n-butyl, cyclobutyl, cyclopentyl, cyclohexyl, cyclohexylmethyl, or cycloheptyl.

It is also preferred that J is phenyl, optionally substituted with one or more halogen substituents. More preferably J is phenyl, p-chlorophenyl, p-fluorophenyl, or m-chlorophenyl.

It is also preferred that J is heteroaryl, 4-pyridyl, aralkyl, benzylthio, or —$CH_2CH_2(NH_2)COOH$.

In other preferred embodiments of the invention the compound of the formula (I) is a compound of the formula (V):

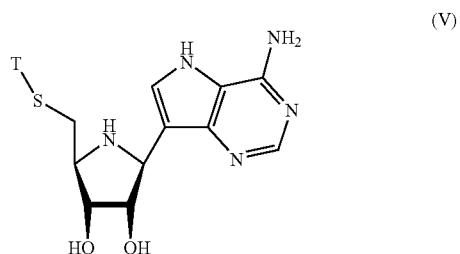
(V)

where T is aryl, aralkyl or alkyl, each of which is optionally substituted with one or more substituents selected from hydroxy, halogen, methoxy, amino, carboxy, and straight- or branched-chain $C_1$-$C_6$ alkyl.

Preferably T is $C_1$-$C_6$ alkyl, optionally substituted with one or more substituents selected from halogen and hydroxy. More preferably T is methyl, ethyl, 2-fluoroethyl, or 2-hydroxyethyl. Most preferably T is methyl.

It is also preferred that T is aryl, optionally substituted with one or more substituents selected from halogen and straight-chain $C_1$-$C_6$ alkyl. More preferably T is phenyl, naphthyl, p-tolyl, m-tolyl, p-chlorophenyl, m-chlorophenyl, or p-fluorophenyl.

It is also preferred that T is aralkyl. More preferably T is benzyl.

Preferably the compound of formula (I) is:
(3R,4R)-1-[(8-aza-9-deazaadenin-9-yl)methyl]-3-hydroxy-4-(hydroxymethyl)pyrrolidine;
(3R,4S)-1-[(9-deazaadenin-9-yl)methyl]-3-hydroxy-4-(2-phenylethyl)pyrrolidine;
(3R,4S)-1-[(9-deazaadenin-9-yl)methyl]-3-hydroxy-4-(benzylthiomethyl)pyrrolidine;
(3R,4S)-1-[(8-aza-9-deazaadenin-9-yl)methyl]-3-hydroxy-4-(benzylthiomethyl)pyrrolidine;
(3R,4S)-1-[(9-deazaadenin-9-yl)methyl]-3-hydroxy-4-(4-chlorophenylthiomethyl)pyrrolidine;

(3R,4R)-1-[(9-deazaadenin-9-yl)methyl]-3-acetoxy-4-(acetoxymethyl)pyrrolidine;
(3R,4S)-1-[(9-deazaadenin-9-yl)methyl]-3-hydroxy-4-(n-butylthiomethyl)pyrrolidine;
(3R,4S)-1-[(9-deazaadenin-9-yl)methyl]-3-hydroxy-4-(4-fluorophenylthiomethyl)pyrrolidine;
(3R,4S)-1-[(9-deazaadenin-9-yl)methyl]-3-hydroxy-4-(n-propylthiomethyl)pyrrolidine;
(3R,4S)-1-[(9-deazaadenin-9-yl)methyl]-3-hydroxy-4-(cyclohexylthiomethyl)pyrrolidine;
(3R,4S)-1-[(9-deazaadenin-9-yl)methyl]-3-hydroxy-4-(3-chlorophenylthiomethyl)pyrrolidine;
(3R,4S)-1-[(9-deazaadenin-9-yl)methyl]-3-hydroxy-4-(ethylthiomethyl)pyrrolidine;
(3R,4S)-1-[(9-deazaadenin-9-yl)methyl]-3-hydroxy-4-(phenylthiomethyl)pyrrolidine;
(3R,4S)-1-[(9-deazaadenin-9-yl)methyl]-3-hydroxy-4-(4-pyridylthiomethyl)pyrrolidine;
(3R,4S)-1-[(9-deazaadenin-9-yl)methyl]-3-hydroxy-4-n-propylpyrrolidine;
(3R,4S)-1-[(9-deazaadenin-9-yl)methyl]-3-hydroxy-4-(homocysteinylmethyl)pyrrolidine;
(3R,4S)-1-[(9-deazaadenin-9-yl)methyl]-3-hydroxy-4-(benzyloxymethyl)pyrrolidine;
(3R,4S)-1-[(9-deazaadenin-9-yl)methyl]-3-hydroxy-4-(i-propylthiomethyl)pyrrolidine;
(3R,4S)-1-[(9-deazaadenin-9-yl)methyl]-3-hydroxy-4-(methoxymethyl)pyrrolidine;
(3R,4S)-1-[(9-deazaadenin-9-yl)methyl]-3-hydroxy-4-(cyclohexylmethylthiomethyl)pyrrolidine;
(3R,4S)-1-[(9-deazaadenin-9-yl)methyl]-3-hydroxy-4-(cycloheptylthiomethyl)pyrrolidine;
(3R,4S)-1-[(9-deazaadenin-9-yl)methyl]-3-hydroxy-4-(cyclopentylthiomethyl)pyrrolidine;
(3R,4S)-1-[(9-deazaadenin-9-yl)methyl]-3-hydroxy-4-(cyclobutylthiomethyl)pyrrolidine.

It is preferred that the cancer prostate cancer or head and neck cancer.

DETAILED DESCRIPTION

Definitions

Figure 1A:
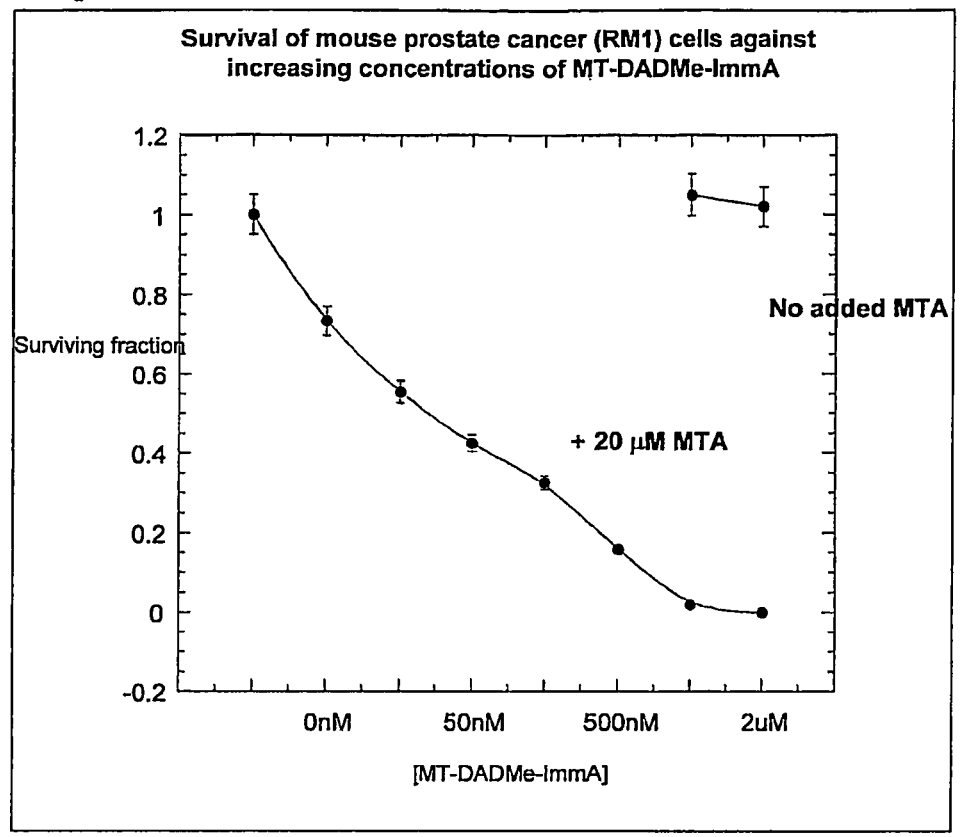
FIG. 1A shows the survival of mouse prostate cancer cells (RM1) against increasing concentrations of compound (2), either in the presence or absence of MTA.

The term "alkyl" is intended to include straight- and branched-chain alkyl groups, as well as cycloalkyl groups. The same terminology applies to the non-aromatic moiety of an aralkyl radical. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group and 1-methyl-2-ethylpropyl group.

The term "aryl" means an aromatic radical having 6 to 18 carbon atoms and includes heteroaromatic radicals. Examples include monocyclic groups, as well as fused groups such as bicyclic groups and tricyclic groups. Some examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "halogen" includes fluorine, chlorine, bromine and iodine.

The compounds are useful for the treatment of certain diseases and disorders in humans and other animals. Thus, the term "patient" as used herein includes both human and other animal patients.

The term "prodrug" as used herein means a pharmacologically acceptable derivative of the compound of formula (I), (IV) or (V), such that an in vivo biotransformation of the derivative gives the compound as defined in formula (I), (IV) or (V). Prodrugs of compounds of formulae (I), (IV) or (V) may be prepared by modifying functional groups present in the compounds in such a way that the modifications are cleaved in vivo to give the parent compound.

Prodrugs include compounds of formulae (I), (IV) or (V), tautomers thereof and/or pharmaceutically acceptable salts thereof, which include an ester functionality, or an ether functionality. It will be clear to the skilled person that the compounds of formulae (I), (IV) or (V) may be converted to corresponding ester or ether prodrugs using known chemical transformations. Suitable prodrugs include those where the hydroxyl groups of the compounds of formula (I), (IV) or (V) are esterified to give, for example, a primary hydroxyl group ester of propanoic or butyric acid. Other suitable prodrugs are alkycarbonyoxymethyl ether derivatives on the hydroxyl groups of the compounds of formula (I), (IV) or (V) to give, for example, a primary hydroxyl group ether with a pivaloyloxymethyl or a propanoyloxymethyl group.

The term "pharmaceutically acceptable salts" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, cam phorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

Discussion of Cancer Treatment

The present invention relates to methods of treating cancer by administering to a patient in need thereof one or more inhibitors of 5'-methylthioadenosine phosphorylase (MTAP). In particular, the invention relates to methods of treating certain cancers, such as prostate cancer or head and neck cancer.

Suitable MTAP inhibitors which may be employed in the method of the present invention and the methods for preparing these inhibitors are described in U.S. Pat. No. 7,098,334 and U.S. Ser. No. 10/524,995.

Certain MTAP inhibitor compounds are surprisingly effective for treating prostate and head and neck cancers. These are compounds of general formula (IV).

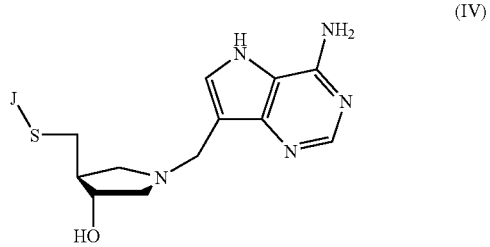

(IV)

This sub-class of MTAP inhibitors incorporates an adenine-like base moiety and a pyrrolidine moiety having an alkyl- aryl- or aralkylthiomethyl group at the 4-position.

Other MTAP inhibitor compounds are also surprisingly effective for treating prostate and head and neck cancers. These are compounds of general formula (V).

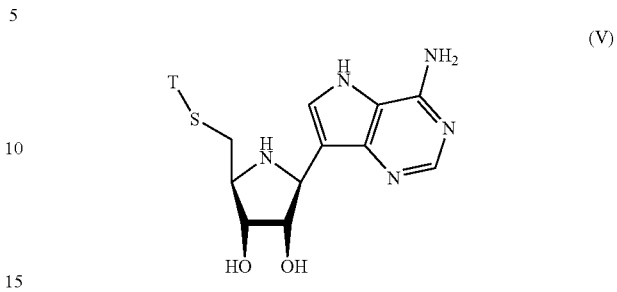

(V)

This sub-class of MTAP inhibitors also incorporates the adenine-like base moiety but has an iminoribitol moiety with an alkyl- aryl- or aralkylthiomethyl group at the 5'-position.

Examples of the first sub-class of inhibitors include compounds (1) and (2).

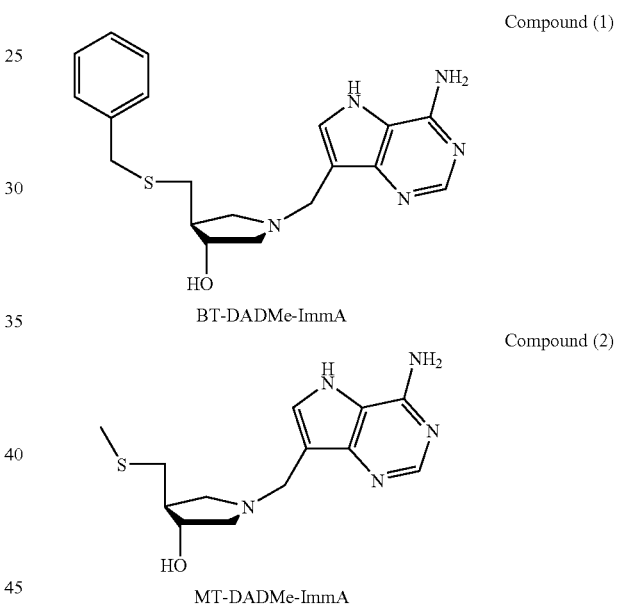

Compound (1)
BT-DADMe-ImmA

Compound (2)
MT-DADMe-ImmA

The Examples below show that compounds (1) and (2) are effective both in vitro and in vivo against a variety of cell lines (PC3, RM1, SCC25 and FaDu). These compounds are therefore particularly useful in the treatment of prostate and head and neck cancers.

The MTAP inhibitor compounds inhibit cell growth in vitro of the prostate cancer cell lines PC3 and RM1 and the head and neck cancer cell lines SCC25 and FaDu. An enhanced cell-killing effect is seen in vitro with combined administration of the MTAP inhibitor compound plus MTA. Examples of this effect are shown in FIGS. 1 to 6.

Furthermore, the inhibitor compounds, when co-administered with MTA, exhibit a cytostatic effect on PC3 cells in vitro.

In order to determine whether the inhibition is selective for malignant cells, normal human fibroblast cells (GM02037) were also treated with compound (2) and MTA for 3 weeks. No cytotoxicity was observed. Compound (2) is therefore cytotoxic for human HNSCC (human head and neck squamous cell carcinoma) cells at doses that exhibit minimal toxicity for normal cells. This selectivity is a further indication that the MTAP inhibitors described above are useful agents for the treatment of head and neck cancer.

The present in vivo studies further demonstrate the surprising efficacy of the compounds. In a NOD-SCID mouse model, compound (2) significantly delays the growth of established FaDu xenografts. The effect is seen either with or without co-administration of the inhibitor compound with MTA.

In addition, prostate cancer progression in the TRAMP mouse model is inhibited in mice treated with compound (2), either alone or in combination with MTA.

An example of the second sub-class of inhibitors is compound (3).

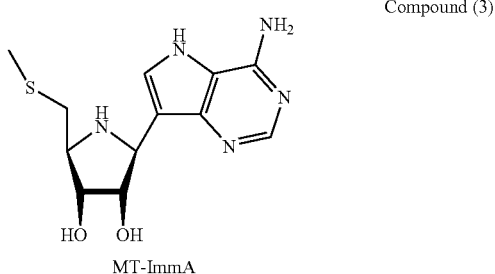

Compound (3)

MT-ImmA

This compound also inhibits prostate cancer progression in the TRAMP mouse model, when administered either alone or in combination with MTA.

For the above in vivo models, the inhibitor compounds exhibit activity when administered with exogenous MTA and when administered alone. There is not a significant enhancement observed when the inhibitors are administered together with MTA. However, the in vitro results clearly demonstrate a surprising enhancement in activity when the inhibitors are administered in conjunction with MTA. Thus, the combined administration method provides a potential alternative treatment method for patients suffering from cancer, where the administration of an MTAP inhibitor is indicated.

The MTAP inhibitor compounds of formulae (I), (IV) and (V) (in particular the compounds of formulae (IV) and (V)) provide an effective alternative treatment option for cancer sufferers, especially for patients diagnosed with prostate and head and neck cancers.

General Aspects

The MTAP inhibitor compounds are useful in both free base form and in the form of salts.

It will be appreciated that the representation of a compound of formula (I) where B and/or D is a hydroxy group, is of the enol-type tautomeric form of a corresponding amide, and this will largely exist in the amide form. The use of the enol-type tautomeric representation is simply to allow fewer structural formulae to represent the compounds of the invention.

Similarly, it will be appreciated that the representation of a compound of formula (I), where B and/or D is a thiol group, is of the thioenol-type tautomeric form of a corresponding thioamide, and this will largely exist in the thioamide form. The use of the thioenol-type tautomeric representation is simply to allow fewer structural formulae to represent the compounds of the invention.

It will also be appreciated that the compounds depicted with bold solid lines are representations of the D-ribo or 2′-deoxy-D-erythro-stereochemical arrangement of substituents on the pyrrolidine ring, such as shown here.

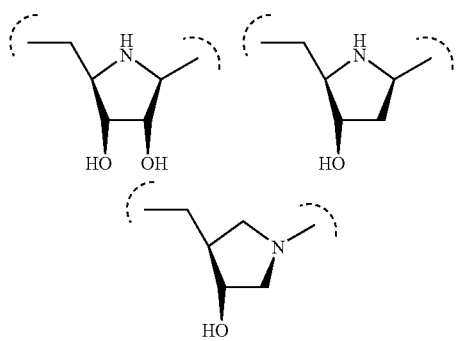

Formulations and Modes of Administration

FIGS. 7, 9, 10, 12, 13, 15 and 16-19 show that the MTAP inhibitor compounds used in the methods of the present invention are orally available, and may therefore be formulated for oral administration. The compounds may also be administered by other routes. For example, the MTAP inhibitors may be administered to a patient orally, parenterally, by inhalation spray, topically, rectally, nasally, buccally or via an implanted reservoir. The amount of compound to be administered will vary widely according to the nature of the patient and the nature and extent of the disorder to be treated. Typically the dosage for an adult human will be in the range less than 1 to 1000 milligrams, preferably 0.1 to 100 milligrams. The specific dosage required for any particular patient will depend upon a variety of factors, including the patient's age, body weight, general health, sex, etc.

For oral administration the active compounds can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil, or a pharmaceutically acceptable surfactant.

The compounds may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

Examples of suitable pharmaceutical carriers are described in Remington's Pharmaceutical Sciences (Mack Publishing Company).

EXAMPLES

Inhibitor Compounds Inhibitors of MTAP were synthesized as described earlier (Singh, V., Shi, W., Evans, G. B., Tyler, P. C., Furneaux, R H, Almo, S C, and Schramm, V L (2004) *Biochemistry* 43, 9-18; Evans G B, Fumeaux R H, Lenz D H, et al., *J Med Chem* 2005:48, 4679-89). Solutions were standardized by the UV absorbance of the 9-deazaadenine ring. Sterile solutions of inhibitors were prepared by filtration.

Protocol for Clonogenic Survival Assay of Cancer Cells 1. 60% confluent plates of experimental cell line was taken and subjected to trypsinization
2. Single cell suspension of the experimental cell line was made in the regular growth medium and number of cells per mililiter of suspension counted
3. A fixed low number of cells were plated out in a volume of 3 ml of growth medium in each well of 6 well culture dishes and incubated overnight at 37° C. in a $CO_2$ incubator
4. Measured volumes of the inhibitor and substrate solutions in sterile deionised cell culture water was added to each well of the 6 well plates. Typically each concentration of inhibitor and/or substrate was added in triplicate wells to calculate error bars. Final concentrations were calculated based on a total volume of 3 ml of culture medium such that dilution factor did not exceed 1% of final volume.
5. Treated cell culture plates were incubated at 37° C. in a $CO_2$ incubator for a period of 7 days
6. At the end of the period of incubation growth medium was removed from each well, attached cells were washed once with PBS and fixed by addition of 100% Formalin solution to each well and keeping at room temperature for ~1 hour.
7. At the end of 1 hour, formalin was removed from the wells and ~150 µL of Crystal Violet staining solution was added to each well and let stand at room temperature for 30 min.
8. After staining is complete, wells were flushed with running tap water to remove traces of residual stain and dried by inverting over paper towels.
9. Number of crystal violet stained colonies in each well containing more than 60 cells per colony was counted.
10. Assuming each colony originated from a single surviving cell post-treatment and taking the number of colonies in the untreated control well as 1, the fraction of surviving cells in each well was calculated and plotted in a graph.

Example 1

Clonogenic Assays (FIGS. 1A and 1B) for Compound (2)

PC3 cells were grown in equal (1:1) portions of Dulbecco's modified Eagle's medium and F12 containing 10% fetal bovine serum, 10 U/mL penicillin-G and 10 µg/mL streptomycin in monolayers to near confluency at 37° C. Cells were lysed in 50 mM sodium phosphate pH 7.5, 10 mM KCl and 0.5% Triton X-100.

Example 2

Figure 2:
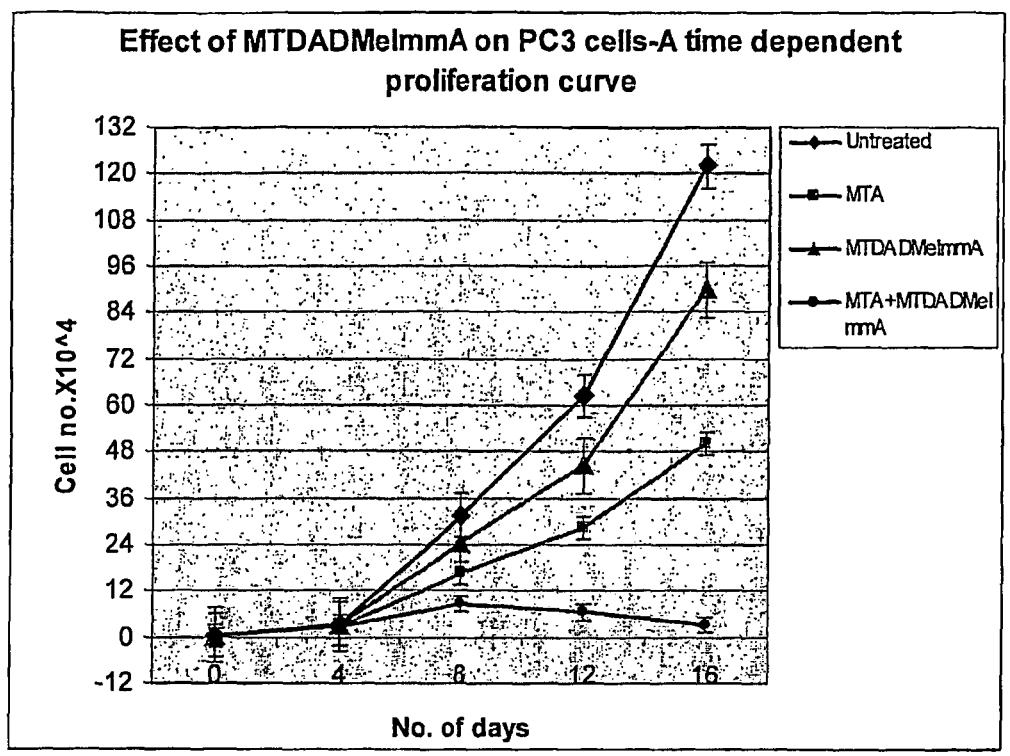
FIG. 2 is a time dependent proliferation curve, showing the effect of compound (2)] and MTA on human prostate cancer cells (PC3).

Effect of Compound 2 and MTA on PC3 Cells (FIG. 2)

PC3 cells were maintained in MEM Eagle's media supplemented with 10% fetal bovine serum, 100 units/ml penicillin, 100 µg/mL streptomycin, 0.1 mM non essential amino acids and 1 mM sodium pyruvate. Cell survival was evaluated using the WST-1 assay (Kicska G A, long Li, Hong H, et al. *Proc Natl Acad Sci USA* 2001; 98:4593-98). Cells were seeded onto 96 well plates at a density of $10^4$ cells per well, with either no additions, 1 µM compound (2), 20 µM MTA or 1 µM compound (2)+20 µM MTA. $IC_{50}$ was determined following the manufacturer's protocol (Roche Applied Science, Ind.). Cells were grown and measured in triplicate or quadruplicate and the error bars show the mean±SD of the multiple samples.

Example 3

Figure 3:
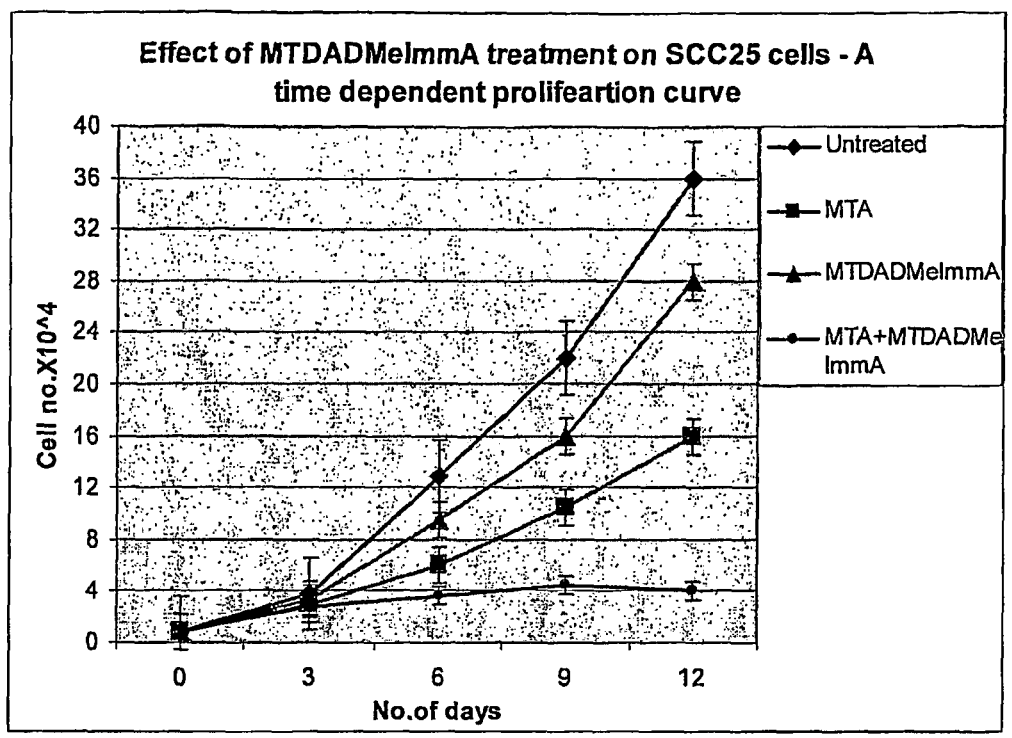
FIG. 3 is a time dependent proliferation curve, showing the effect of compound (2) and MTA on SCC25 cells.

Effect of Compound 2 and MTA on SCC25 Cells (FIG. 3)

SCC25 cells were maintained in MEM Eagle's media supplemented with 10% fetal bovine serum, 100 units/ml penicillin, 100 µg/mL streptomycin, 0.1 mM non essential amino acids and 1 mM sodium pyruvate. Cell survival was evaluated using the WST-1 assay (Kicska G A, long Li, Hong H, et al. *Proc Natl Acad Sci USA* 2001; 98:4593-98). Cells were seeded onto 96 well plates at a density of $10^4$ cells per well, with either no additions, 1 µM MT-compound (2), 20 µM MTA or 1 µM compound (2)+20 µM MTA. $IC_{50}$ was determined following the manufacturer's protocol (Roche Applied Science, Ind.). Cells were grown and measured in triplicate or quadruplicate and the error bars show the mean±SD of the multiple samples.

Example 4

Figure 4:
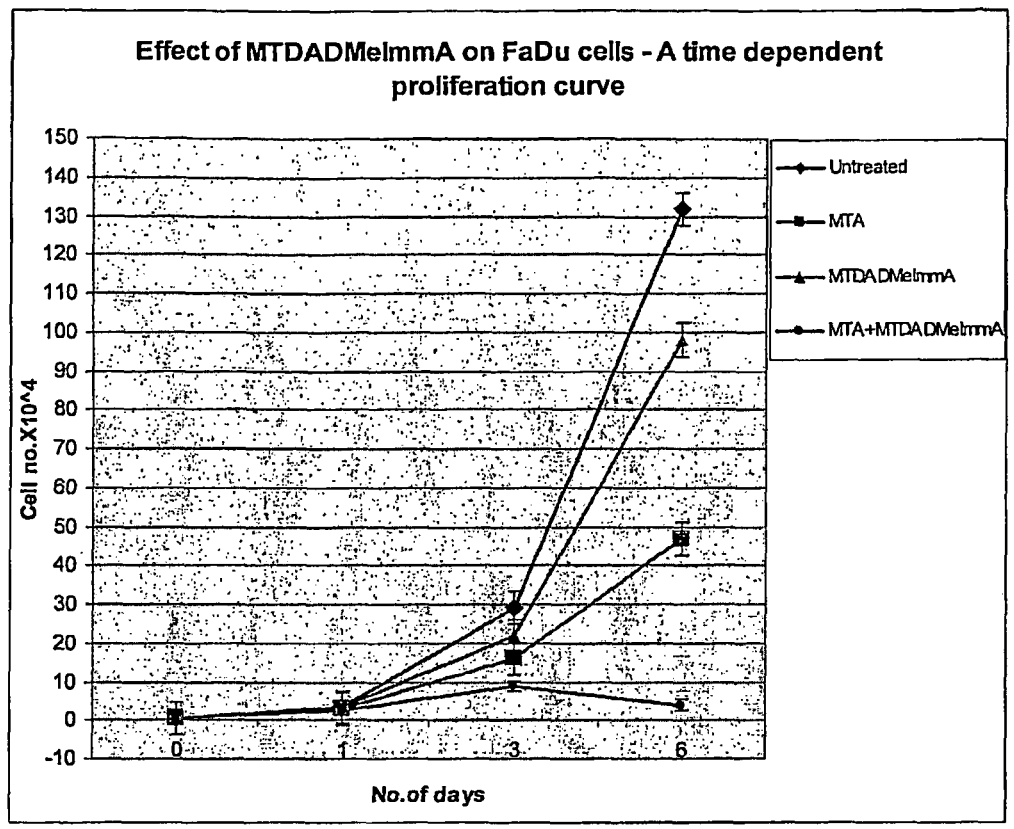
FIG. 4 is a time dependent proliferation curve, showing the effect of compound (2) and MTA on FaDu cells.

Effect of MT-DADMe-ImmA (Compound (2)) and MTA on FaDu Cells (FIG. 4)

FaDu cells were maintained in MEM Eagle's media supplemented with 10% fetal bovine serum, 100 units/ml penicillin, 100 µg/mL streptomycin, 0.1 mM non essential amino acids and 1 mM sodium pyruvate. Cell survival was evaluated using the WST-1 assay (Kicska G A, long Li, Honig H, et al. *Proc Natl Acad Sci USA* 2001; 98:4593-98). Cells were seeded onto 96 well plates at a density of $10^4$ cells per well, with either no additions, 1 µM compound (2), 20 µM MTA or 1 µM compound (2)+20 µM MTA, $IC_{50}$ was determined following the manufacturer's protocol (Roche Applied Science, Ind.). Cells were grown and measured in triplicate or quadruplicate and the error bars show the mean±SD of the multiple samples.

Example 5

Figure 5:
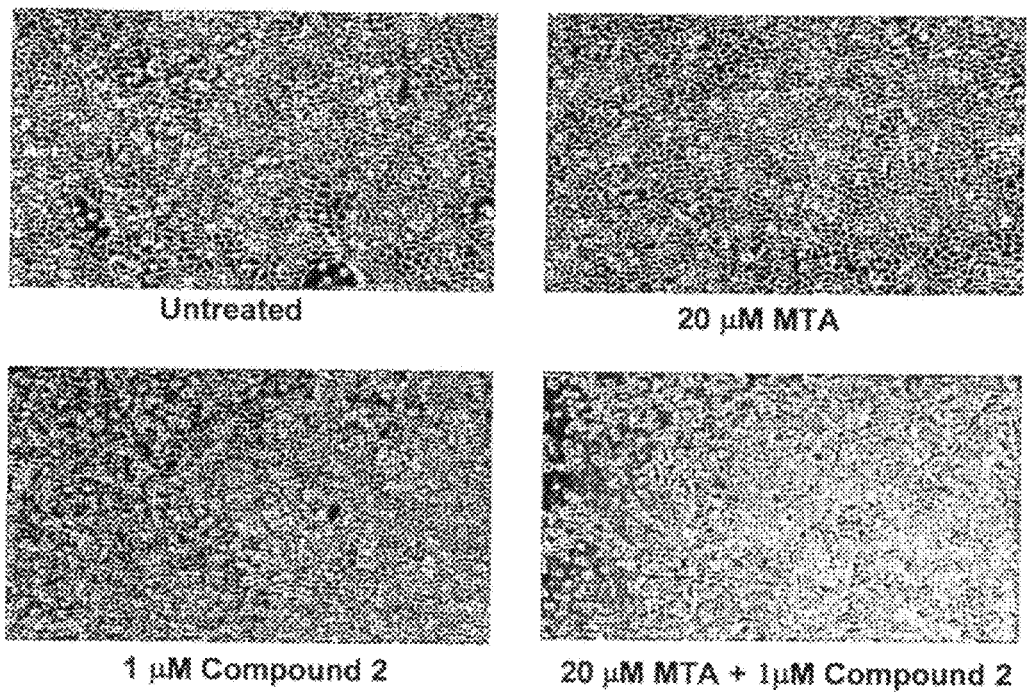
FIG. 5 shows phase contrast photographs of FaDu cells after 5 days of treatment with compound (2) and MTA.

Phase Contrast Microscopy of FaDu Cells (FIG. 5)

FaDu cells were subjected to six days in culture using the same conditions described as for Example 4.

Example 6

Figure 6:
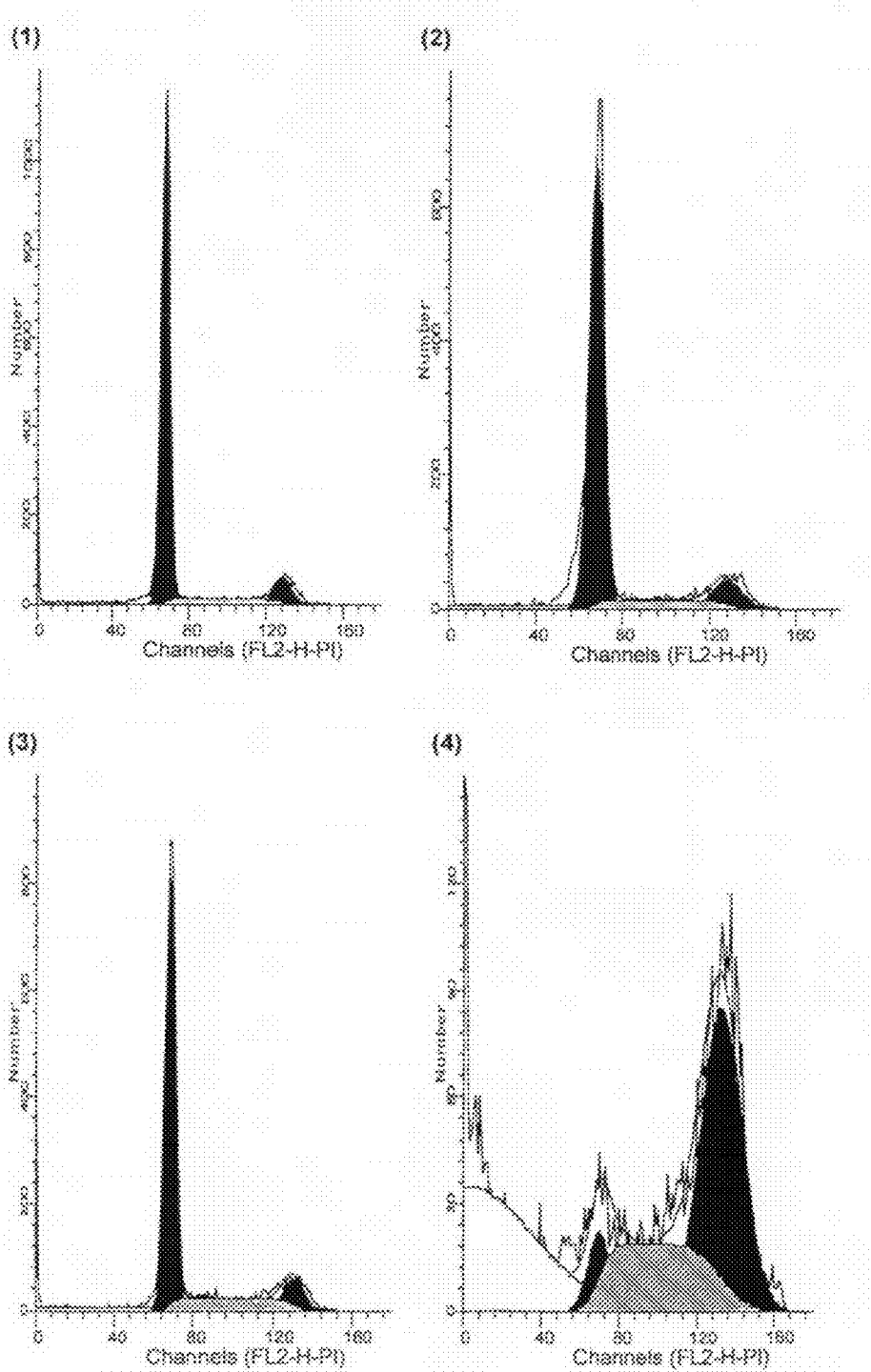
FIG. 6 shows a cell cycle and apoptosis analysis of FaDu cells after 6 days of treatment with compound (2) and MTA; (1) untreated results: G1 83.66%, S 8.08%, G2 8.26%, Apoptosis 6.06%; (2) treated with MTA results: G1 79.67%, S 10.42%, G2 9.91%, Apoptosis 6.66%; (3) treated with compound (3) results 01 72.06%, S 17.98%, G29.96%, Apoptosis 7.89%; (4) treated with MTA+compound (3) results G1 8.26%, S 31.25%, G2 60.49%, Apoptosis 29.41%.
Figure 7:
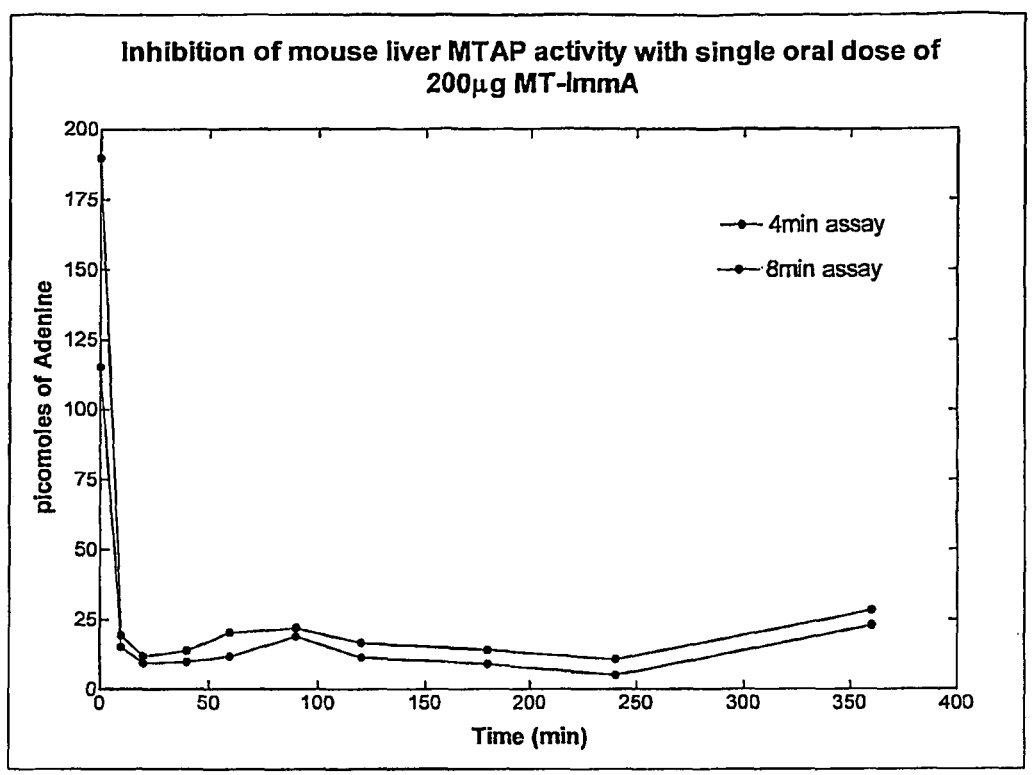
FIGS. 7 to 19 show oral and IP availability of selected compounds that may be used in the methods of the invention, including for compounds (1)-(3) and for ethylthio-DADMe-ImmA, para-chlorophenylthio-DADMe-ImmA, para-fluorophenylthio-DADMe-ImmA, phenylthio-DADMe-ImmA, and phenylthio-ImmA.
Figure 8:
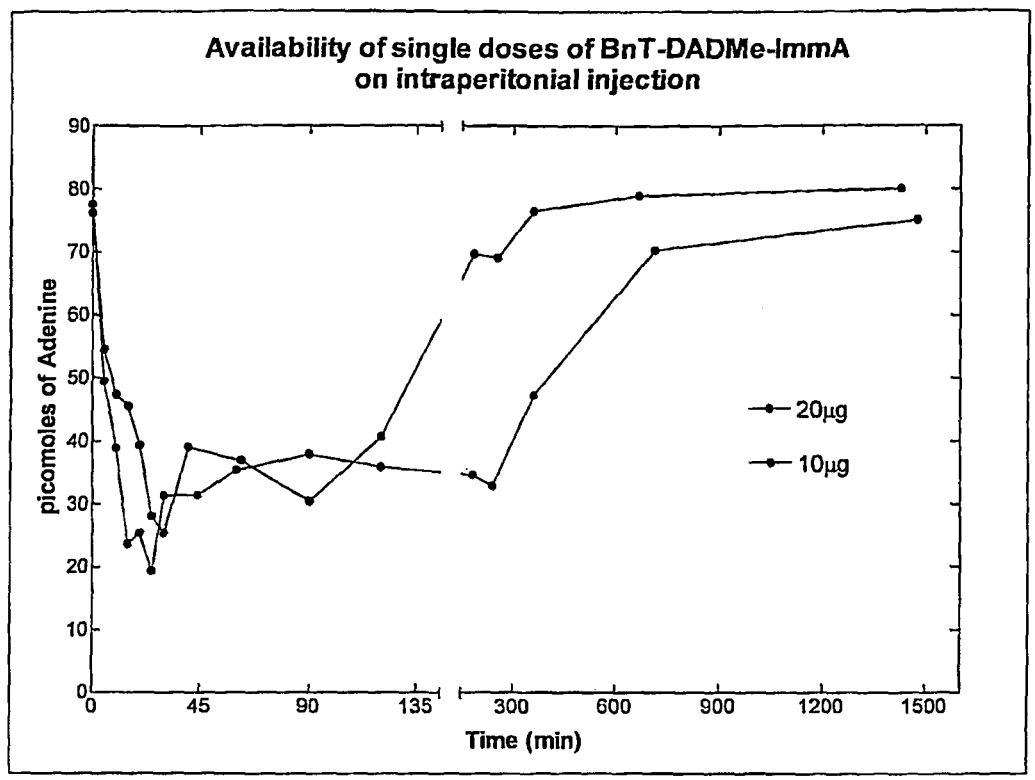
Figure 9:
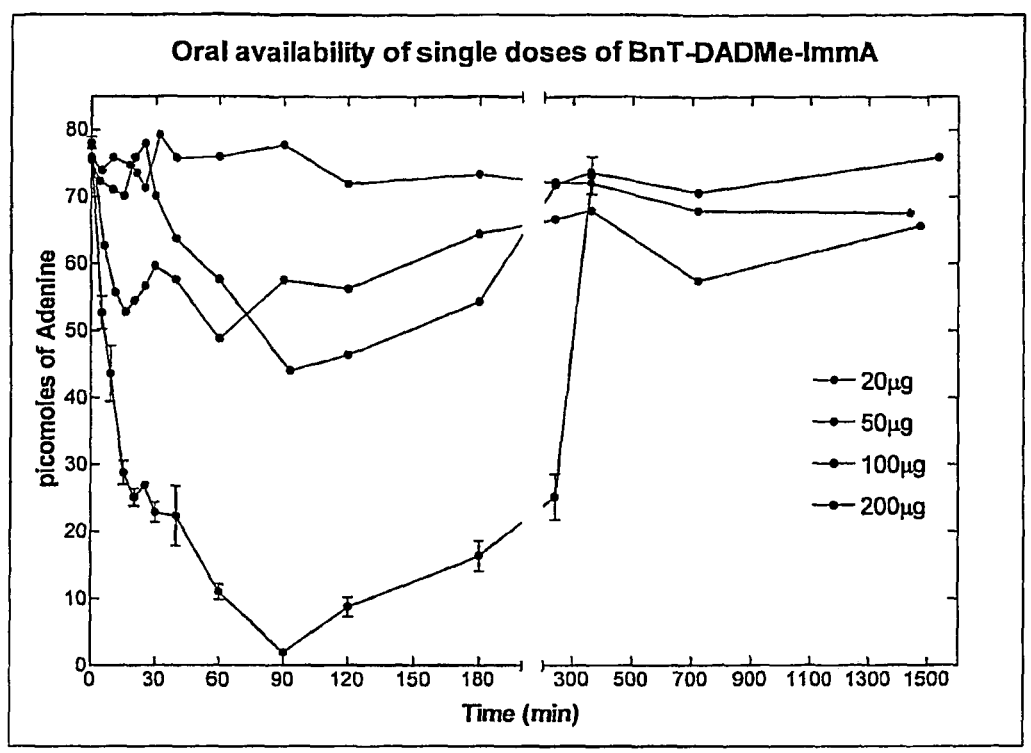
Figure 10:
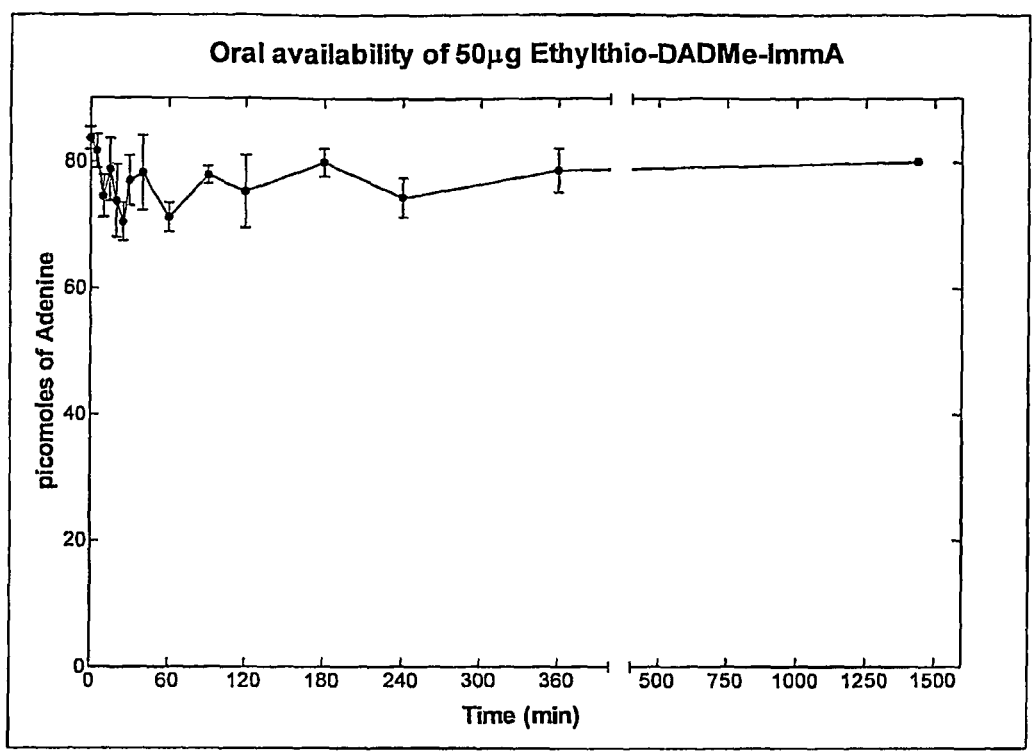
Figure 11:
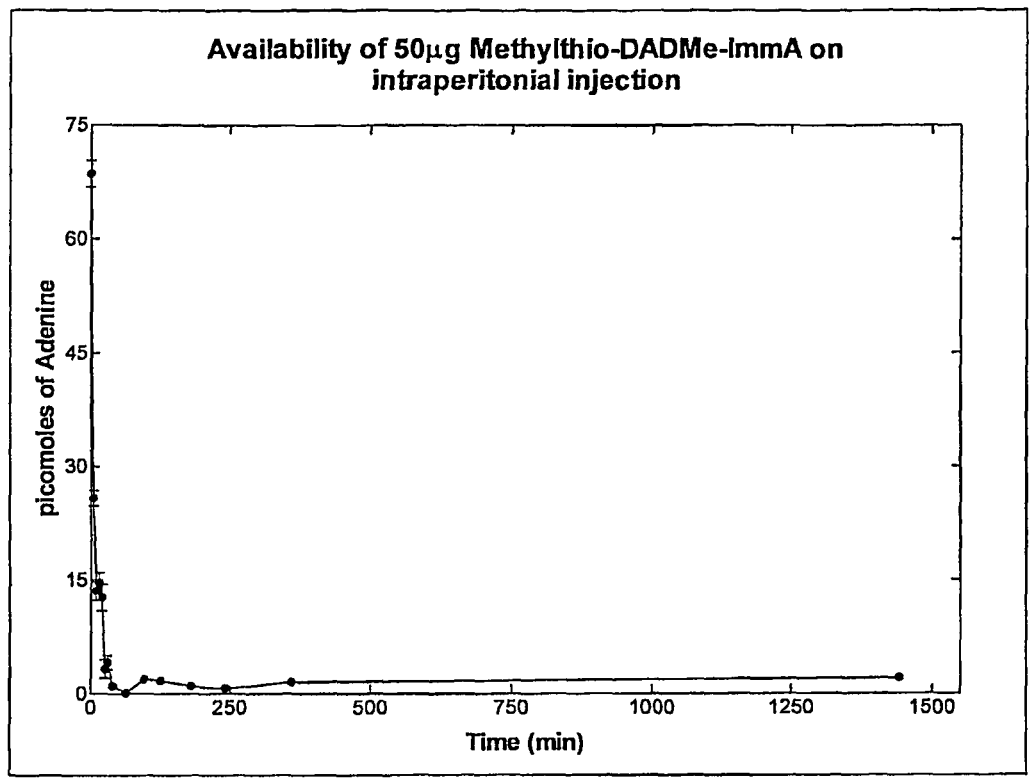
Figure 12:
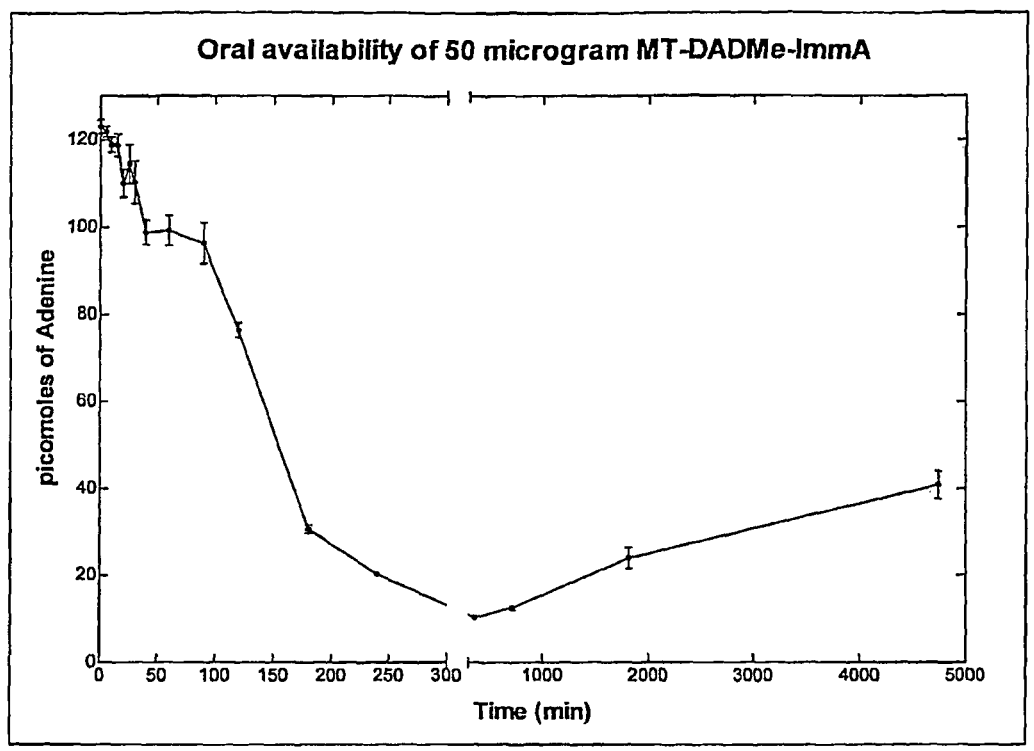
Figure 13:
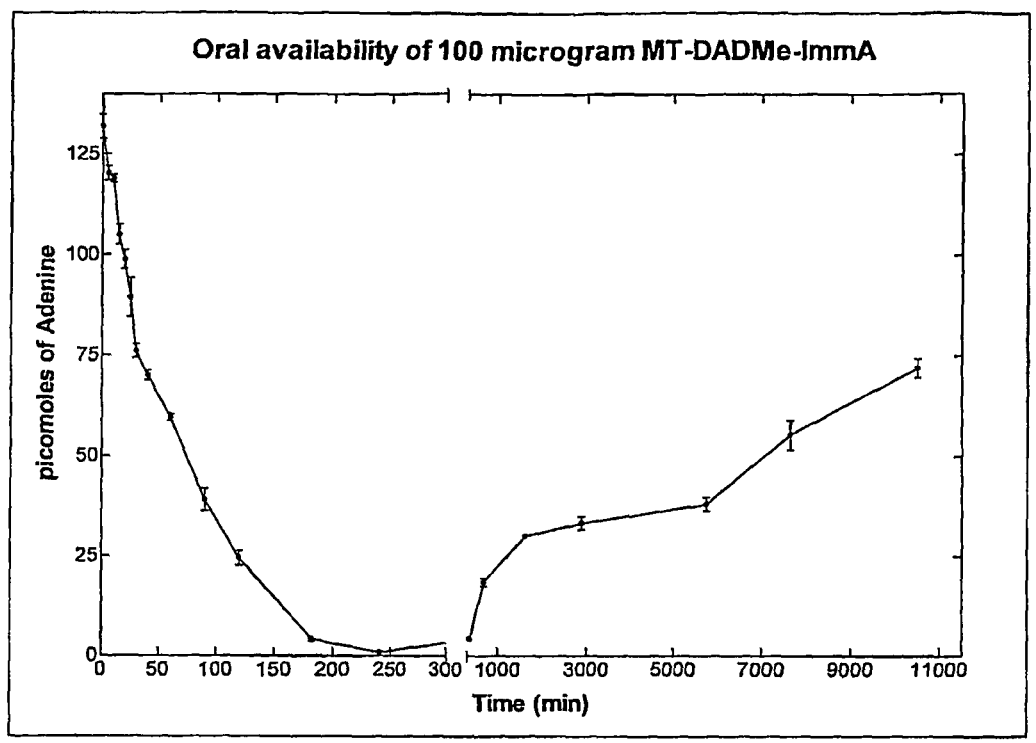
Figure 14:
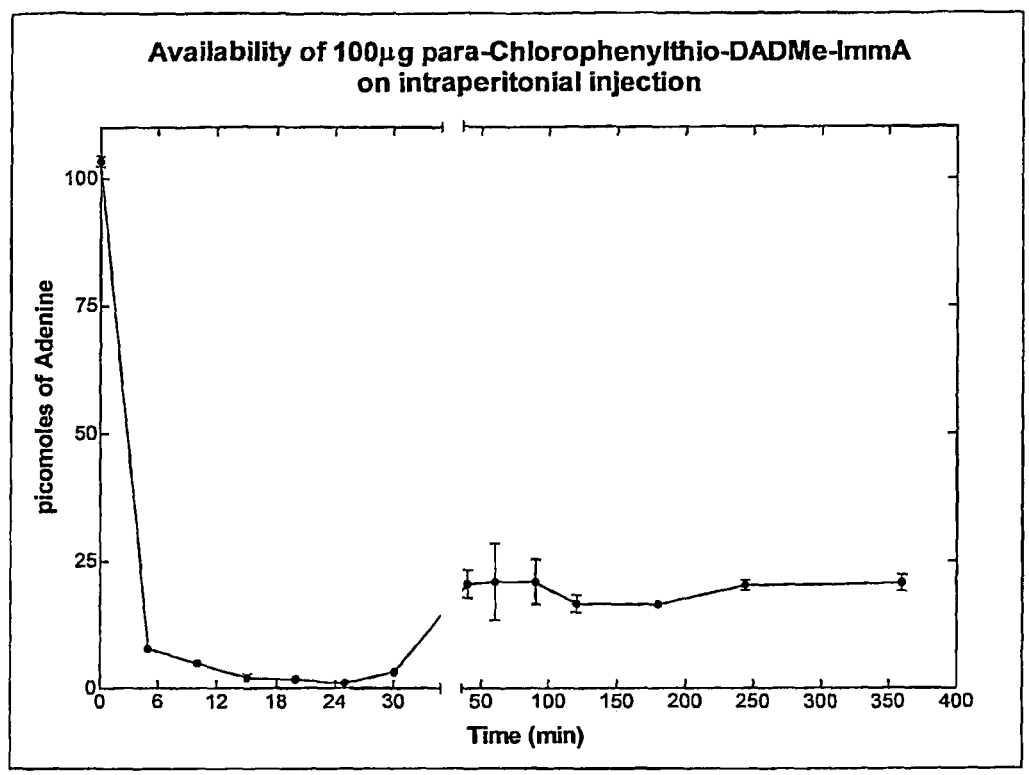
Figure 15:
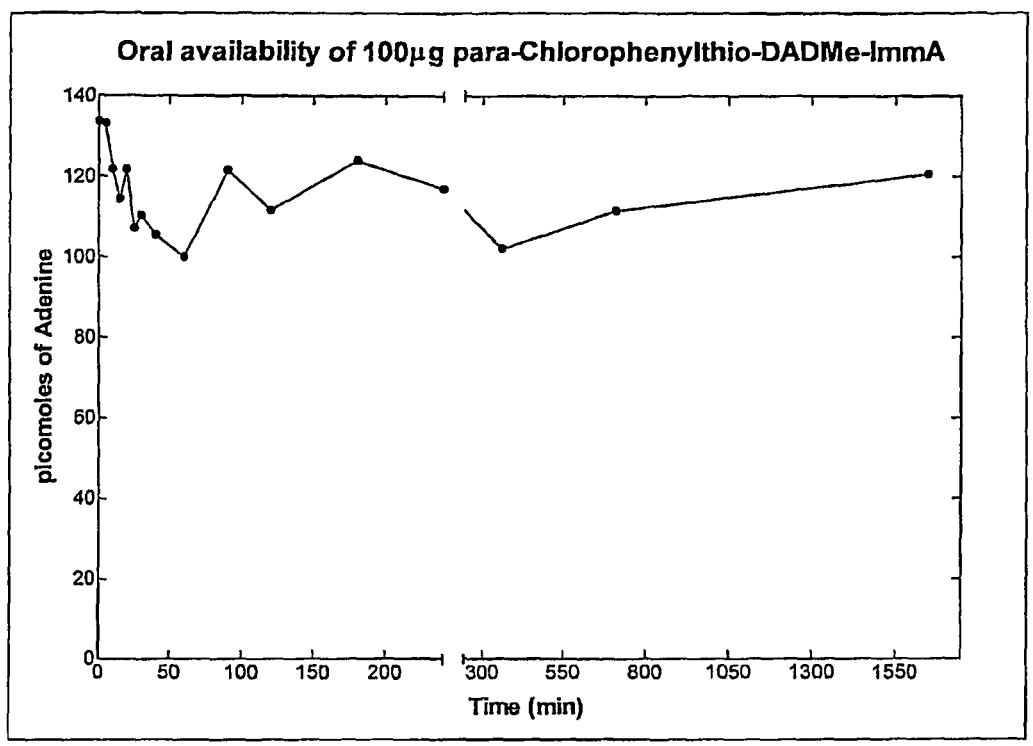
Figure 16:
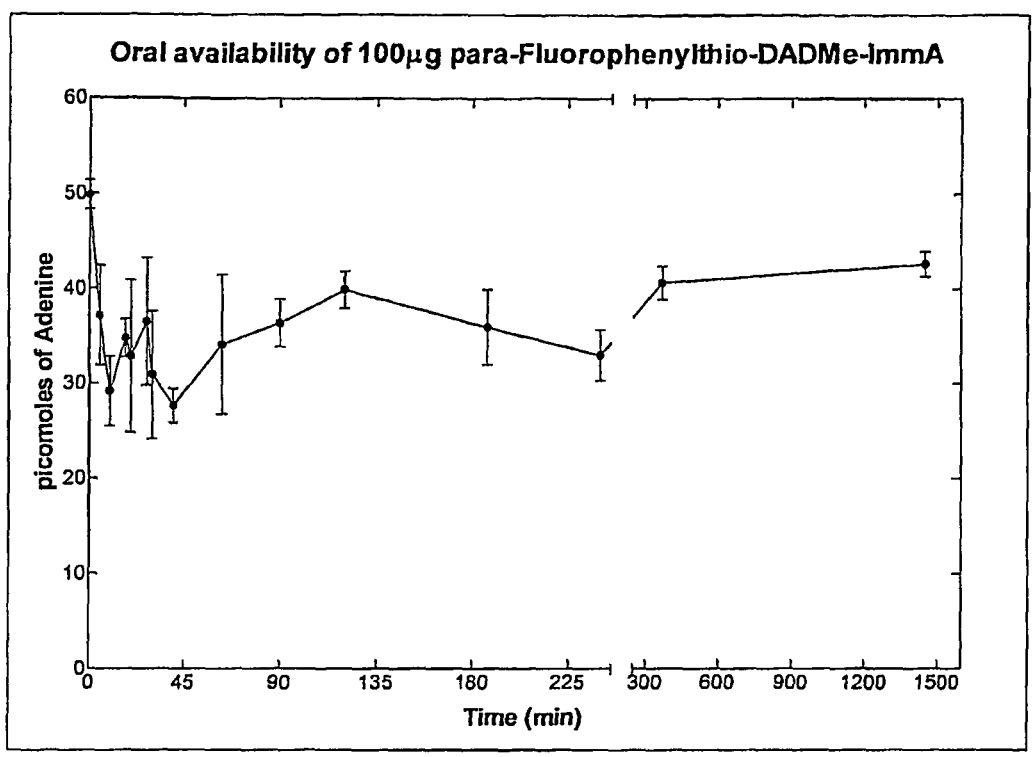
Figure 17:
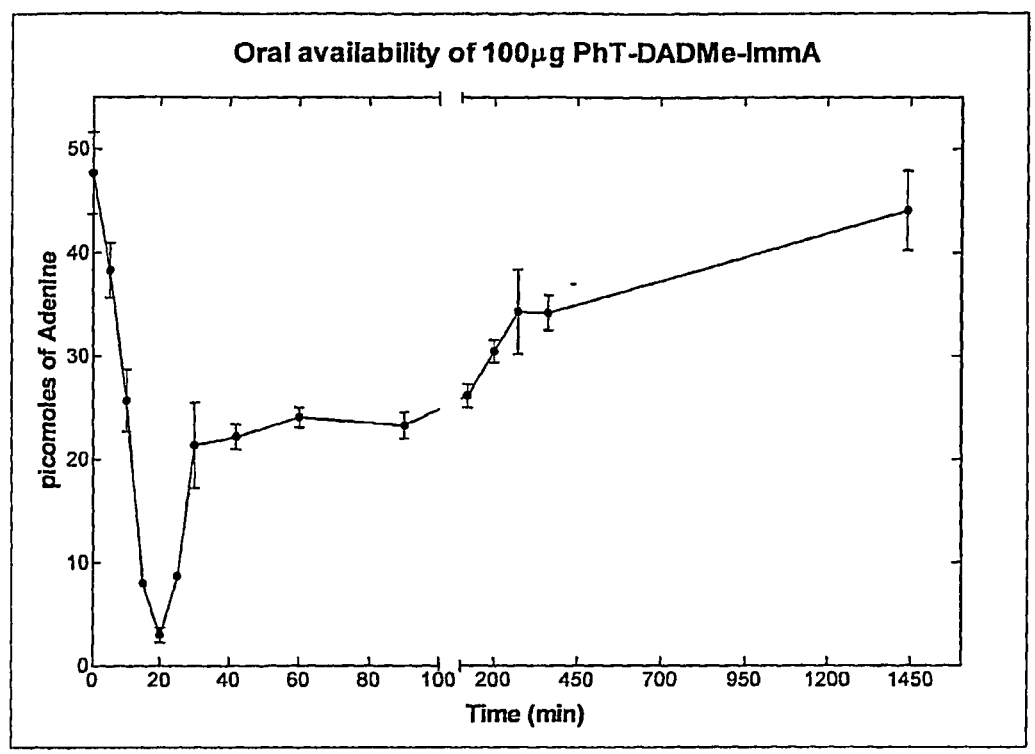
Figure 18:
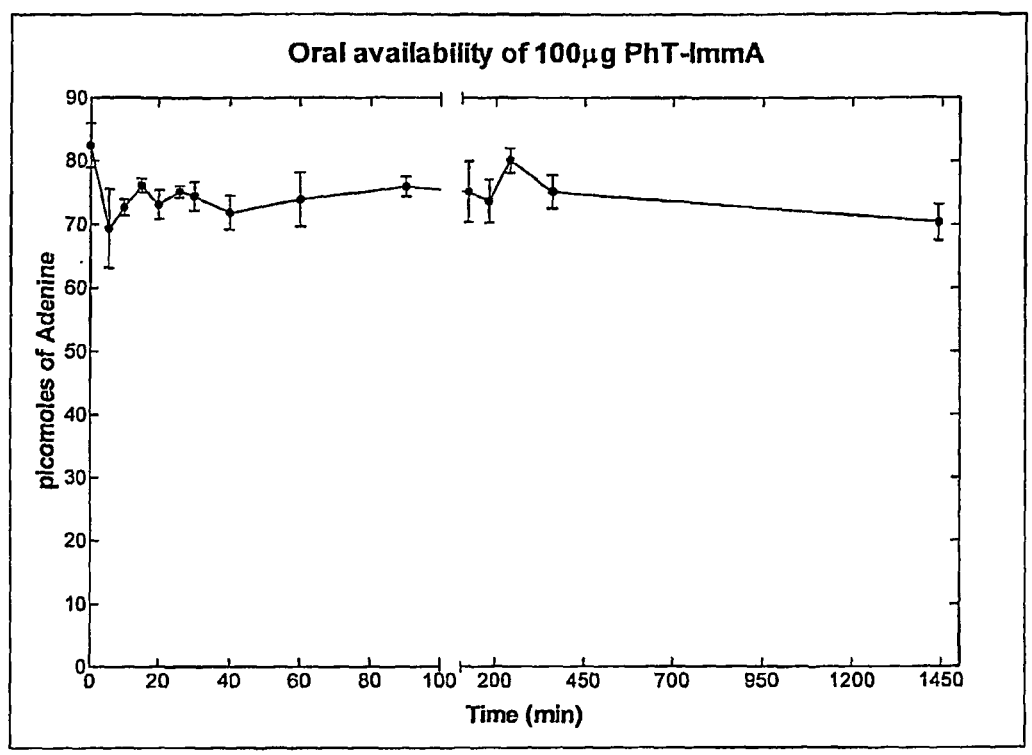
Figure 19:
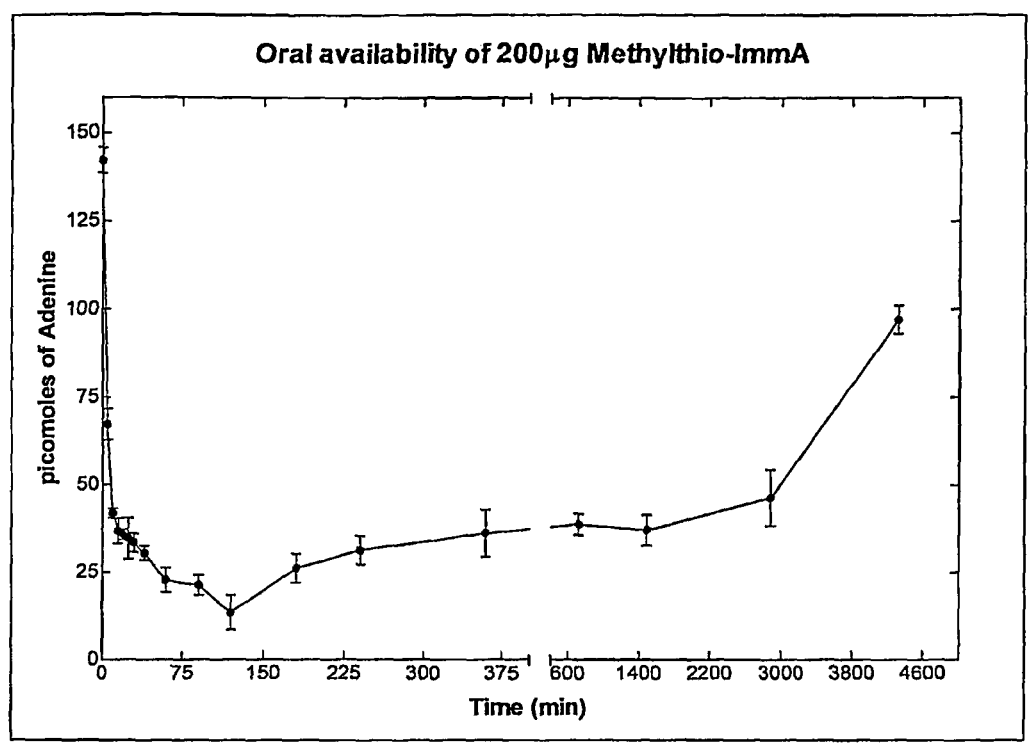

Cell Cycle and Apoptosis Analysis of FaDu Cells (FIG. 6)

FaDu cells were subjected to six days in culture using the same conditions described as for Example 4, before staining with propidium bromide and FACS cell sorting analysis.

Example 7

Oral Availability (Compound (2))

Two groups of 3 C57BL6 mice received a single oral dose of compound (2) dissolved in sterile, deionized water, pippeted onto a crumb of food. Treated food was fed to each mouse individually under close observation at time zero. Two different single doses of inhibitor were administered: 50 µg and 100 µg. Mice were individually fed and closely observed for consumption of food. At specific time points, 4 µL blood samples were collected from the tail vein. The blood was mixed with 4 µL 0.6% Triton X-100 in PBS and stored at −80° C. until time of analysis. The amount of adenine produced was measured by the following MTAP activity assay: Cells were harvested, washed three times with PBS and lysed with RIPA buffer. The reaction mixture for MTAP activity assays contained the following: ~75 µg protein from cell lysates, 50 mM HEPES pH 7.4, 50 µM MTA, and 20,000 dpm [2.8-3H] MTA. Labeled MTA was synthesized from [2.8-3H]S-adenosylmethionine by a known method. Products of the MTAP reaction were resolved using TLC silica plates with 1 M ammonium acetate, pH 7.55, and 5% isopropanol. Adenine spots were excised and counted for label incorporation.

Example 8

Oral and IP Availability for Selected Compounds (FIGS. 7 to 19)

Oral dosing was performed in essentially the same manner as for Example 7. For IP availability, 100 µg of the inhibitor was dissolved in around 200 µl of sterile deionised water and taken up in a 1 ml syringe attached to a 26G needle and injected intraperitonially in the mouse at 0 min time point. Blood (4 µl) was collected from the tail of the mouse at specific time points, mixed with 4 µl of 0.6% TritonX-100 solution in PBS and stored at −80° C. until ready for enzyme assay. Blood (4 µl) was collected from each mouse prior to injection which served as 0 min control time point. Each experiment was repeated three times with three different mice to get standard error bars.

Example 9

Figure 20:
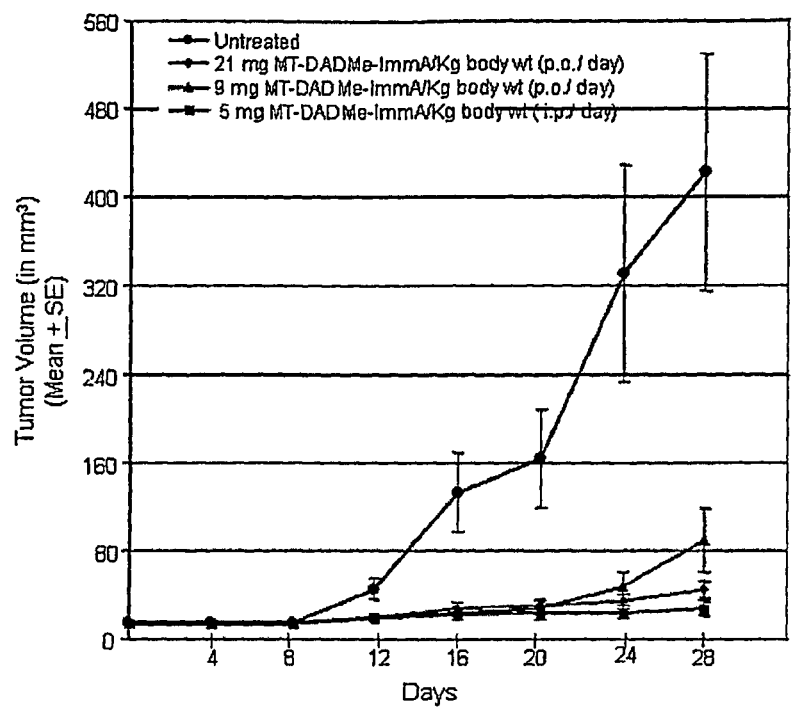
FIG. 20 shows the effects of compound (2) on FaDu xenografts in NOD-SCID mice.
Figure 21:
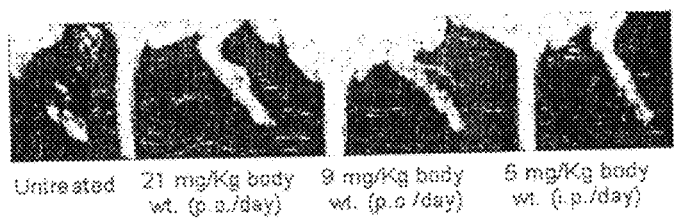
FIG. 21 shows representative tumours from each of the treatment cohorts for the above NOD-SCID mouse study.

FaDu Xenograft Studies (FIGS. 20 and 21)

NOD-SCID mice (6-8 weeks old) were obtained from Jackson Laboratory (Bar Harbor, Me.). FaDu cells ($10^6$) were inoculated into the dorsum of the hind foot. After 5 days, mice were treated with 9 mg/kg or 21 mg/kg body weight of compound (2) in drinking water or by daily i.p. injections of 5 mg/kg body weight of compound (2). After inoculation mice were assigned to treatment or control groups (n=5). Tumor volume (V) was determined from: V=(4/3)*(22/7)*1/8* (length*width*height). Differences between treatment cohorts were determined using the Student's t test. Mice were weighed every 4-5 days, monitored for hair loss, loss of appetite, vomiting and diarrhea. Total and differential blood and bone marrow analyses were performed after treatment with compound (2).

Example 10

Figure 22:
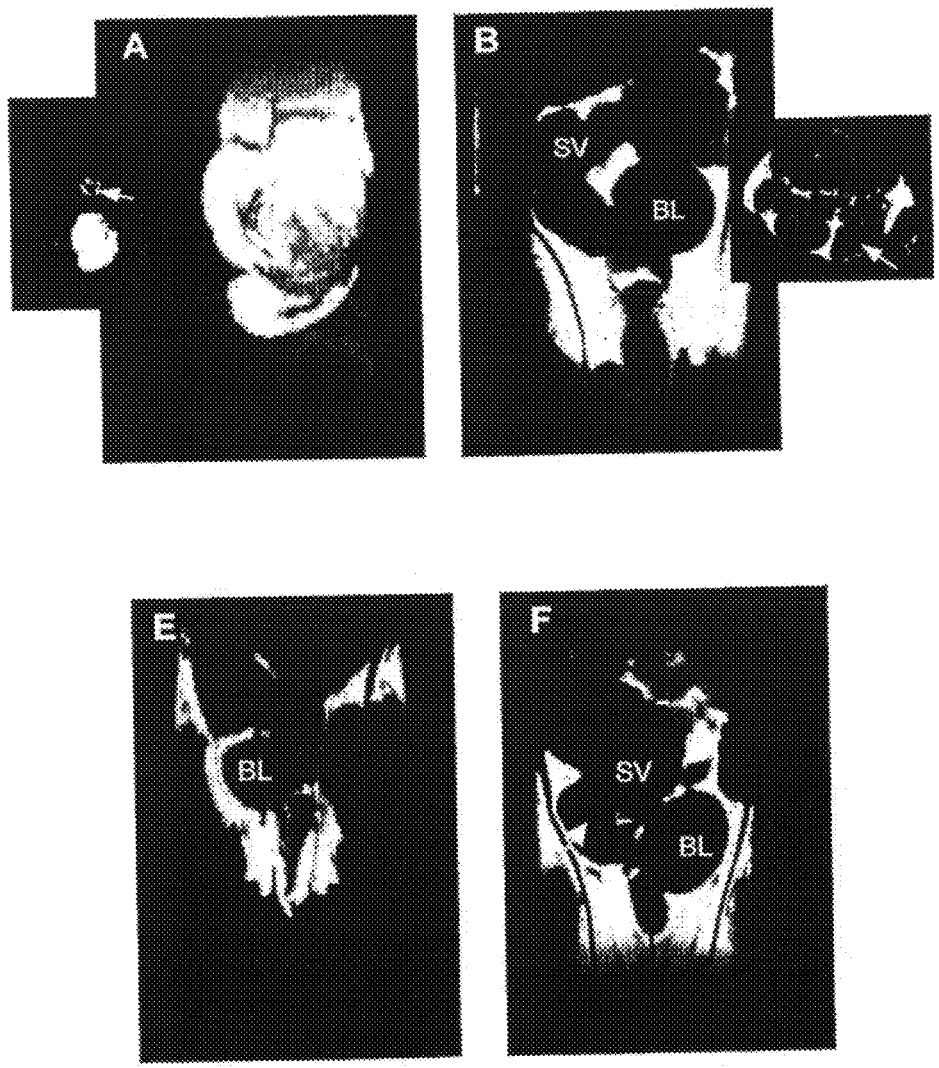
FIG. 22 shows MRI images of TRAMP mice (Panels A and B: Control TRAMP (transgenic adenocarcinoma of mouse prostate) mice, Panels E and F: TRAMP mice treated with 1 mM compound (2).

MRI Studies (FIG. 22)

MRI experiments were performed using a 9.4T 21 cm bore horizontal bore magnet (Magnex Scientific) Varian INOVA MRI system (Fremont, Calif.) equipped with a 28 mm inner diameter quadrature birdcage coil. Mice were anesthetized with isoflurane inhalation anesthesia (1-1.5% in 100% $O_2$ administered via a nose cone) and positioned in the MRI coil. Body temperature was maintained (37-38° C.) using a homeothermic warming system. After acquiring scout images, multi-slice spin-echo imaging with an echo time of 18 ms and a repetition time of 400 ms ms was performed. A 40 mm field of view with a 256×256 matrix size was used. Nine to 15 slices along the transverse, sagittal, and coronal planes were acquired in each multi-slice experiment with a slice thickness of 1 mm and the gap between slices of 0.5 mm. MRI data were processed off-line with MATLAB-based MRI analysis software.

Example 11

Figure 23:
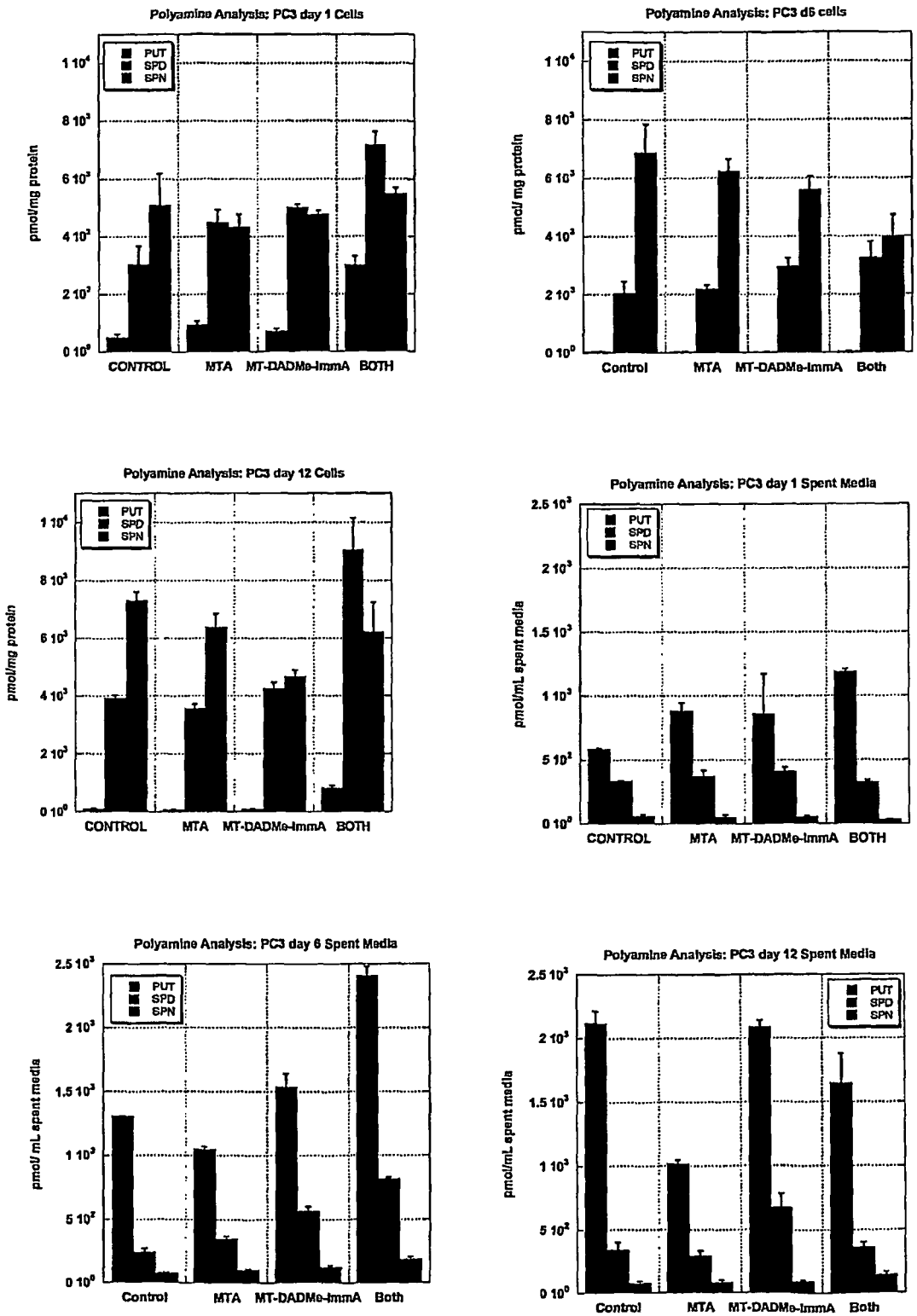
FIG. 23 shows that compound (2) and MTA alter polyamine levels and induce cytostasis in PC3 cells (PUT=putrescine, SPD=spermidine, SPN=spermine). PC3 cells were cultured and treated in triplicate as follows: untreated control, 20 μM substrate (MTA) alone, 1 μM compound (2) alone, or a combination of both substrate and inhibitor. Both cells and spent media were harvested at 1, 6, and 12 days for polyamine analysis by HPLC fluorescence.

Quantitation of Polyamines in Cells, Spent Media and Tissue Samples (FIG. 23)

Spent media and perchloric acid extracts of both PC3 cells and tissue samples were subjected to purification via cation exchange chromatography and dansyl-derivatized with minor changes. Disposable 10 ml BIO-RAD columns were centrifuged at 4,000 rpm for 3 minutes. Sodium carbonate used for derivatization was adjusted to pH 9.3 and the concentration of dansyl-chloride was adjusted to 100 mM. Dansyl-polyamines were quantitated by a Waters HPLC/Fluorescence system. A Phenomenex Luna 5µ C18 column was used with a mobile phase of 30% acetonitrile in a 50 mM ammonium acetate buffer at pH 6.8 (eluent A) and 100% acetonitrile (eluent B). Fluorescence detection was monitored by excitation at 338 nm and emission at 500 nm.

Example 12

Treatment of TRAMP Mice (Table 1, FIG. 22)

Short-Term: Mice were treated with sterile solutions of 100 µM compound (2) (pH ~6.4). Water bottles were autoclaved prior to filling with sterile inhibitor solutions. Mice were sacrificed at 1, 2, and 7 days, with three mice in each group, with the control group sacrificed after 7 days. Livers were immediately removed upon sacrifice for polyamine analysis, conducted as described above.

Long-Term: Sterile solutions of 100 µM compound (2) (pH ~6.4). Water bottles were autoclaved prior to filling with sterile inhibitor solutions. Water consumption was monitored every other day, with fresh inhibitor solution being administered to prevent bacterial growth. Mice were control-sacrificed and tissues (genitourinary system, liver, lungs) were collected for histology and polyamine analysis. Mass and dimensions of excised genitourinary system tumours were recorded. Sections of small intestine were also removed for toxicity analysis via H&E staining.

Example 13

Figure 26:
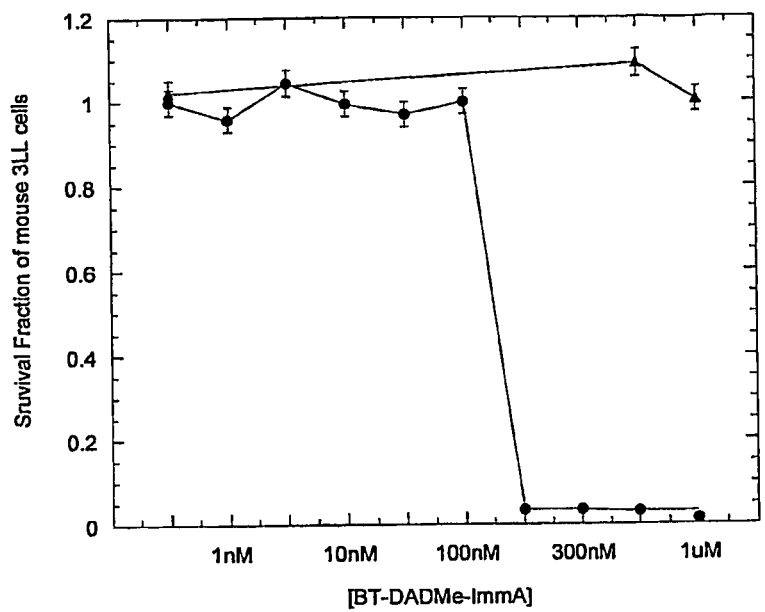
FIG. 26 shows mouse lung cancer cells in culture responding to compound (1) in the presence of 20 μM MTA and not responding in the absence of MTA.

Mouse 3LL Cell Studies for Compound (1) (FIG. 26)

Growth of 3LL and RM1 cells was in Dulbecco's modified Eagle's medium containing serum and antibiotics with 5 mM sodium pyruvate and 0.25 mM non essential amino acid mixture (Gibco). Compound (1) was added as a sterile solution and MTA was absent or present at 20 μM.

Discussion of the Examples

Figure 1B:
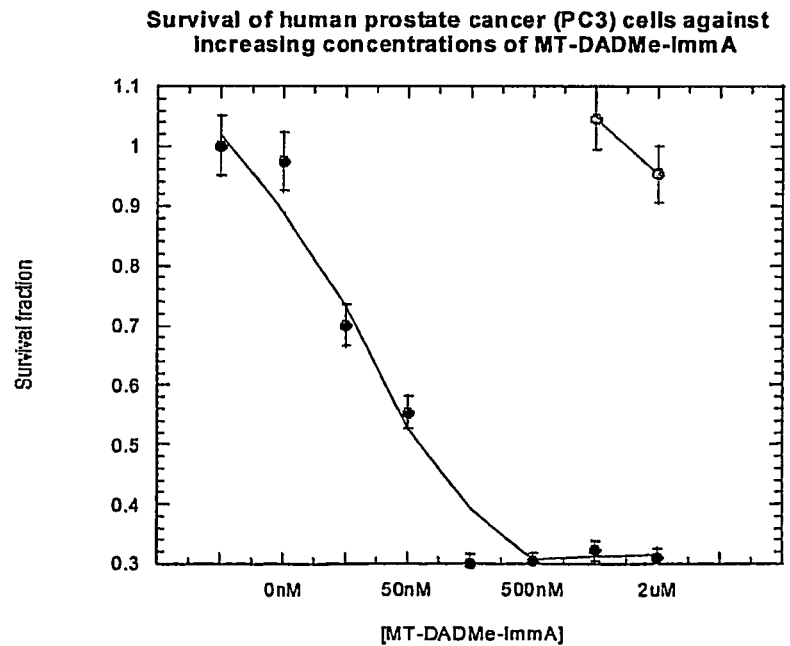
FIG. 1B shows the survival of human prostate cancer cells (PC3) against increasing concentrations of compound (2), either in the presence or absence of MTA.

FIG. 1A shows the effect of the addition of compound (2) to cultured mouse prostate cancer cells (RM1). FIG. 1B shows the effect of the addition of compound (2) to cultured human prostate cancer cells (PC3). Compound (2) was added either alone or in the presence of 20 μM MTA. FIGS. 2, 3 and 4 show the effects of MTA alone, compound (2) alone, and MTA with compound (2) in time dependent cell proliferation experiments (PC3 cells, SCC25 cells and FaDu cells). The combination of compound (2) and MTA reduces cell proliferation. These data demonstrate that the compounds which are used in the methods of the present invention inhibit cell growth in vitro, when administered in combination with MTA.

FIG. 5 further demonstrates, showing phase contrast photographs of FaDu cells after 5 days of treatment with compound (2)/compound (2)+MTA, that the inhibitor compound+MTA is effective in inhibiting cell growth.

Thus, administration of MTA in circumstances where its degradation by MTAP is inhibited by an MTAP inhibitor leads to greater circulatory and tissue levels of MTA and consequently an enhanced effect in the treatment of cancer.

FIG. 6 shows that compound (2) in combination with MTA is also effective for stopping cell cycling (for FaDu cells) such that the cells become apoptotic.

FIGS. 7 to 19 show oral and IP availability of selected compounds, including compounds (1)-(3) and ethylthio-DADMe-ImmA, para-chlorophenylthio-DADMe-ImmA, para-fluorophenylthio-DADMe-ImmA, phenylthio-DADMe-ImmA, and phenylthio-ImmA.

FIGS. 20 and 21 show the results of in vivo studies. The time-dependent growth of FaDu tumors in immunodeficient mice was suppressed by oral or intraperitoneal treatment with compound (2) (FIG. 20). Tumors were established in mice for 5 days prior to oral or interperitoneal treatments with compound (2). Tumor growth in animals treated with compound (2) was dose responsive and was significantly slower than in controls (p<0.06). Representative tumors from the treatment cohorts are shown at 28 days after therapy began (FIG. 21). No significant differences in animal weight or in total and differential blood counts were seen between treatment and control groups after this treatment. Thus, compound (2) administration suppresses FaDu growth in vivo with low cytotoxicity. Subsequent to the 28 day compound (2) therapy, treatment was removed for a subsequent period of 28 days. There was no regrowth of tumor in those mice receiving the two highest doses of compound (2).

Figure 25A:
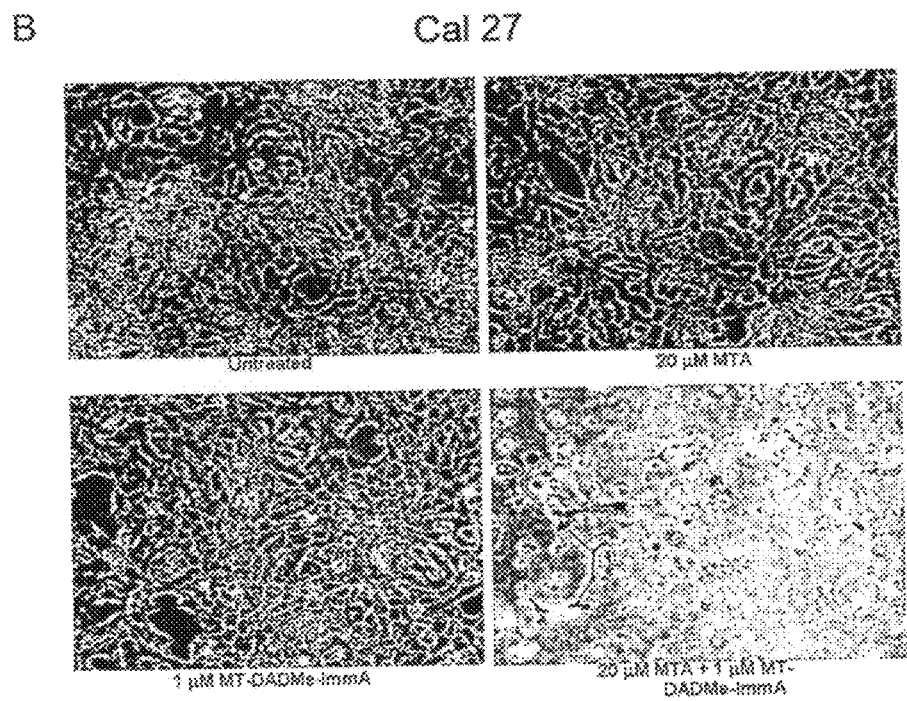
FIGS. 25A and 25B show Cal27 cells grown for 8 days as control (untreated), in the presence of 20 μM MTA, 1 μM compound (2) alone or in combination (1 μM compound (2)+20 μM MTA).
Figure 25B:
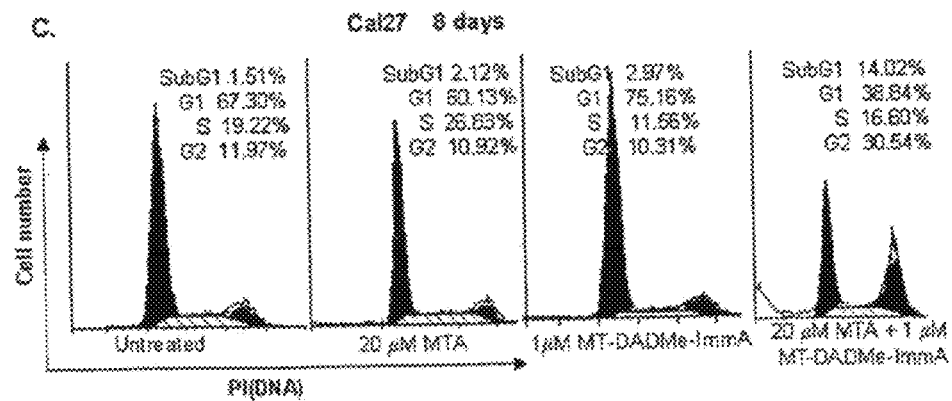

Another head and neck cancer cell line, Cal27 was also found to be susceptible to compound (2) and MTA. After 8 days of treatment, the number of viable Cal27 cells decreased as a result of $G_2$/M arrest and apoptosis when compared to controls (FIGS. 25A and 25B).

Longitudinal MRI provides a noninvasive means of monitoring prostate tumour growth in mice (Gupta S, Hastak K, Ahmad N, Lewin J S, Mukhtar H *Proc Natl Acad Sci USA* 2001 Aug. 28; 98(18):10350-5; Eng M H, Charles L G, Ross B D, Chrisp C E, Pienta K J, Greenberg N M, Hsu C X, Sanda M G Urology 1999 December:54(6):1112-9; Song S K, Qu Z, Garabedian E M, Gordon J I, Milbrandt J, Ackerman J J *Cancer Res.* 2002 Mar. 1:62(5):1555-8.).

MRI was used to evaluate prostate tumour growth and progression longitudinally in TRAMP mice (either untreated or treated with a compound that may be used according the methods of the invention). Mice were imaged approximately monthly from 12-33 weeks of age. Representative MRI images comparing untreated control TRAMP and treated TRAMP mice at approximately 30 weeks of age are shown in FIG. 22.

Panels A and B show results from control mice. Panel A shows a coronal section through of a 30 week old TRAMP mouse with a large tumour (bright tissue) that weighed 8.76 g upon dissection at 34 weeks of age. The inset shows a more posterior coronal section. The bright tumour is smaller in this section but metastasis to the liver is observed (white arrow). Panel B shows a coronal section through the prostate region of a 30 week old TRAMP mouse. The seminal vesicles (SV) are enlarged. A large tumour (weighing 4.89 g upon dissection at 36 weeks of age) that spanned from the kidney to bladder (BL) is visible in the transverse section shown in the inset (white arrow).

Panels E and F show results for mice treated with 1 mM compound (2). Panel E shows a coronal section through the prostate region of a 30 week old treated TRAMP mouse. The tumour, weighing 0.41 g upon dissection at 34 weeks of age, was not observed during the imaging session. Panel F shows a similar section through a 30 week old treated TRAMP mouse that exhibited a 0.64 g tumour upon dissection at 39 weeks of age. The tumour is indicated by the white arrow in the MRI image shown in this panel.

Untreated TRAMP mice therefore demonstrate primary prostate tumour growth. However, prostate cancer progression in the TRAMP mouse is inhibited in mice treated with compound (2), either alone or in combination with MTA.

FIG. 23 shows that compound (2) and MTA, administered together, alter polyamine levels and induce cytostasis in PC3 cells. Combination treatment of PC3 cells with compound (2) and MTA for 1 day resulted in a significant 6-fold increase in intracellular PUT levels ($3.03 \times 10^{-3} \pm 2.86 \times 10^{-2}$, combination treated cells vs. $5.04 \times 10^{-2} \pm 1.08 \times 10^{-2}$, control, p=0.0001, pmoles PUT/mg protein), a 2-fold increase in spent media PUT levels [$1.19 \times 10^3 \pm 2.04 \times 10^{-1}$, combination treated media vs. $5.85 \times 10^{-2} \pm 5.09 \times 10^{-0}$, control media, p=0.0001, pmoles PUT/mL spent media, as well as roughly a 2.5-fold increase in intracellular SPD levels ($7.19 \times 10^{-3} \pm 4.38 \times 10^{-2}$, combination treated cells vs. $3.05 \times 10^{-3} \pm 6.3 \times 10^{-2}$, control p=0.001 pmoles SPD/mg protein). SPN levels in combination treated spent media also slightly decreased (p=0.02). After 6 days of treatment, cellular SPN levels were decreased roughly 0.5-fold ($4.0 \times 10^{-3} \approx 7.38 \times 10^{-2}$, combination treated cells vs. $6.87 \times 10^{-3} \pm 9.68 \times 10^{-2}$, control, p=0.005, pmoles SPN/mg protein), with both PUT and SPD elevated (p=0.02 and p=0.01, respectively in comparison to controls). Most significantly, levels of PUT in spent media were almost double that of the control ($2.41 \times 10^{-3} \pm 7.35 \times 10^{-1}$, combination treated spent media vs. $1.31 \times 10^{-3} \pm 0.0$, control, p=0.0007, pmoles PUT/mL spent media). By day 12, a significant increase in cellular SPD levels were observed ($9.05 \times 10^{-3} \pm 1.09 \times 10^{-3}$, combination treated cells vs. $3.93 \times 10^{-3} \pm 8.4 \times 10^{-1}$, control, p=0.007, pmoles SPD/mg protein), with a corresponding decrease in levels of spent media PUT levels ($1.65 \times 10{-3} \pm 2.27 \times 10^{-2}$, combination treated spent media vs. $2.12 \times 10^{-3} \pm 9.34 \times 10^{-1}$, control media, pmoles PUT/mL spent media, p=0.013). Intracellular PUT levels in combination treated cells were still significantly higher than controls (p=0.005).

Treatment of PC3 cells with compound (2) resulted in numerous significant alterations in both intracellular and spent media polyamine levels. After 24 hours of treatment, the increase observed in cellular SPD levels as well as putrescine (PUT) cellular and spent media polyamine levels correlated with the effects expected with MTAP inhibition. MTA accumulated in the cells, began feedback inhibition of SPN synthase, resulting in accumulations of SPD and PUT, with PUT being significantly excreted into the media, and a slight decrease of SPN in the media. By day 6, cellular SPN levels were significantly reduced in combination treated cells, while maintaining the characteristic elevations in levels of PUT and SPD. Treatment of cells for 12 days showed a significant increase in cellular SPD levels and a slight decrease in spent media PUT levels, pointing to the fact that a compensatory pathway had been activated to make up for the block in MTAP. PUT may have been being taken up from the media for SPD synthesis. After combination treatment for approximately 2 weeks, PC3 cells displayed a cytostatic effect, as determined by the clonogenic assay. Initially, it was believed that MTAP inhibition would lead to MTA accumulation, causing feedback inhibition of polyamine biosynthesis, resulting in decreases in cellular proliferation. Although a halt in cellular proliferation was observed, this is clearly not due simply to polyamine depletion.

Figure 24A:
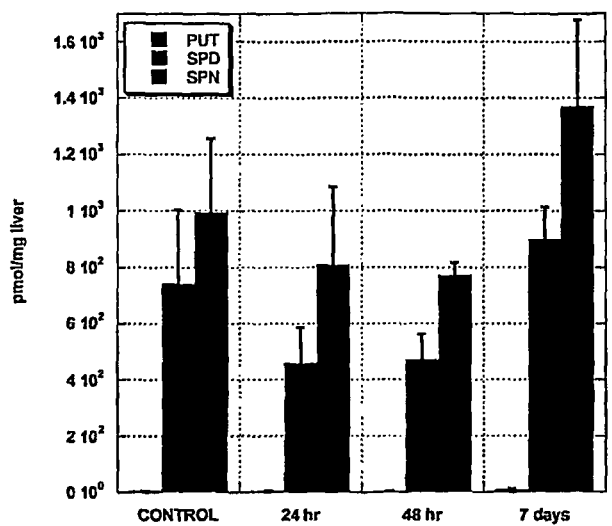
FIGS. 24A, 24B and 24C show that compound (2) reduces tumour growth and metastasis in TRAMP mice, but does not alter polyamine levels in vivo. C56Bl/6 mice were treated with 100 μM compound (2) via their drinking water and sacrificed at 24, 48 hours, and 7 days. Livers were immediately removed for polyamine analysis. TRAMP mice were treated approximately 6-8 months with 100 μM compound (2) via their drinking water and control sacrificed. Livers were removed for polyamine analysis.
Figure 24B:
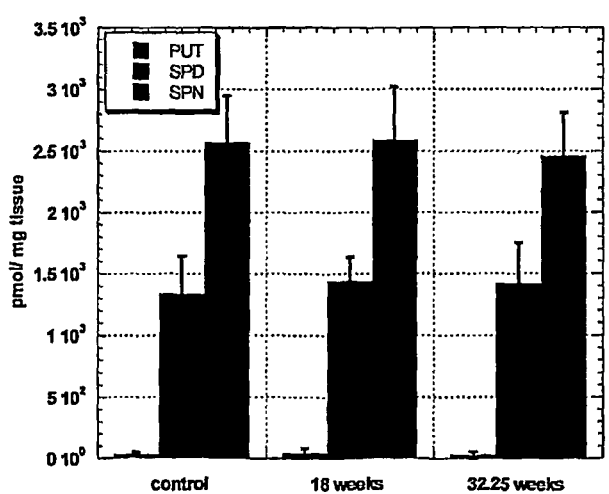
Figure 24C:
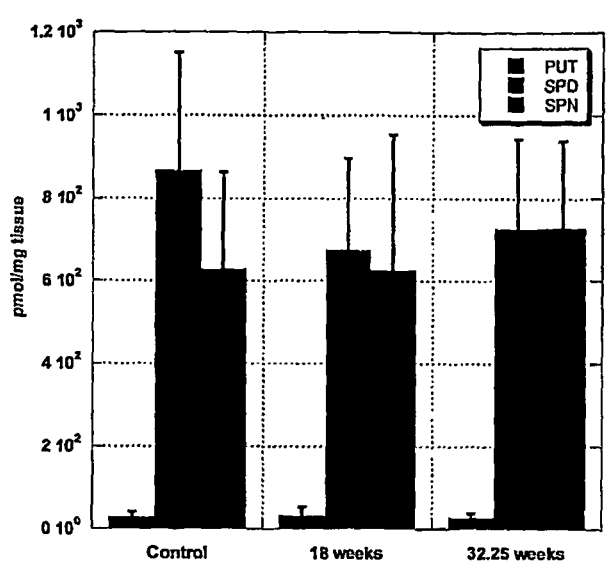

FIGS. 24A-C show that compound (2) reduces tumour growth and metastasis in TRAMP mice, but does not alter polyamine levels in vivo. Polyamine levels of mice livers were not significantly altered during short-term treatment (FIG. 24A). After extended treatment with compound (2) inhibitor solutions, no significant alterations in either TRAMP liver or GUS polyamine levels were detected (FIGS. 24B and 24C).

Mass (Table 1) and dimensions of excised genitourinary system tumors were recorded for all members of the treatment groups. Sections of small intestine were also removed for toxicity analysis via H&E staining. Histology of TRAMP mice revealed all animals showed extensive prostate intraepithelial neoplasia involving most prostate acini. However, the size and incidence of preinvasive tumors, as well as the incidence of invasive cancer and metastasis were all decreased in treated TRAMP mice (Table 1). No alterations, inflammations, or irregularities were observed in the intestinal crypts, neither were any hair loss or general GI problems noted, indicating a lack of drug toxicity.

TABLE 1

Summary of results for TRAMP mice treated with compound (2)

| Experimental Condition | # Animals (n) | Tumor Size (g) | Weeks treated | Metastatic Cancer |
|---|---|---|---|---|
| Control | 16 | 4.0 ± 2.8 | 32 ± 5 | 44% |
| 100 µM compound (2) | 12 | 1.7 ± 0.8 | 29 ± 7 | 8% |

FIG. 26 shows mouse lung cancer cells in culture responding to compound (1) in the presence of 20 µM MTA and not responding in the absence of MTA. This establishes that the effect of the inhibitor is on MTAP and that cancer cell lines are susceptible to this treatment.

Although the invention has been described by way of example, it should be appreciated the variations or modifications may be made without departing from the scope of the invention. Furthermore, when known equivalents exist to specific features, such equivalents are incorporated as if specifically referred to in the specification.

INDUSTRIAL APPLICABILITY

Compounds that are inhibitors of MTAP inhibitors have potential for treating cancer, particularly prostate cancer and head and neck cancer.

The invention claimed is:

1. A method of treating a prostate cancer or a head and neck cancer or a lung cancer in a patient in need thereof comprising administering to the patient with a prostate cancer or a head and neck cancer or a lung cancer a compound of formula (I) in an amount effective to kill cancer cells in a patient, wherein formula (I) is:

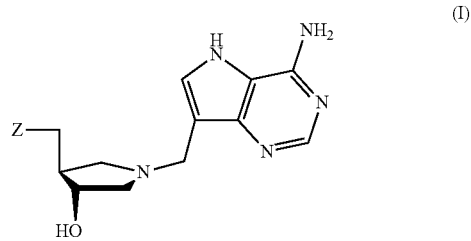

where Z is selected from SQ and Q, where Q is alkyl, aralkyl or aryl, each of which is optionally substituted with one or more substituents selected from hydroxy, halogen, methoxy, amino, and carboxy, or a pharmaceutically acceptable salt thereof, or an ester thereof.

2. A method as claimed in claim 1 where Z is SQ.

3. A method as claimed in claim 2 where Z is not methylthio.

4. A method as claimed in claim 2 where Q is an alkyl group, optionally substituted with one or more substituents selected from hydroxy, halogen, methoxy, amino, and carboxy.

5. A method as claimed in claim 4 where the alkyl group is a $C_1$-$C_6$ alkyl group.

6. A method as claimed in claim 2 where Q is an aryl group, optionally substituted with one or more substituents selected from hydroxy, halogen, methoxy, amino, and carboxy.

7. A method as claimed in claim 6 where the aryl group is a phenyl or benzyl group.

8. A method as claimed in claim 1 where any halogen is chlorine or fluorine.

9. A method as claimed in claim 1 where Q is methyl, ethyl, n-propyl, i-propyl, n-butyl, cyclobutyl, cyclopentyl, cyclohexyl, cyclohexylmethyl, or cycloheptyl.

10. A method as claimed in claim 1 where Q is phenyl, optionally substituted with one or more halogen substituents.

11. A method as claimed in claim 1 where Q is phenyl, p-chlorophenyl, p-fluorophenyl, or m-chlorophenyl.

12. A method as claimed in claim 1 where Q is heteroaryl, 4-pyridyl, aralkyl, benzylthio, or —$CH_2CH_2(NH_2)COOH$.

13. A method as claimed in claim 1 where the compound of formula (I) is:

(3R,4S)-1-[(9-deazaadenin-9-yl)methyl]-3-hydroxy-4-(2-phenylethyl)pyrrolidine;

(3R,4S)-1-[(9-deazaadenin-9-yl)methyl]-3-hydroxy-4-(benzylthiomethyl) pyrrolidine;

(3R,4S)-1-[(9-deazaadenin-9-yl)methyl]-3-hydroxy-4-(4-chlorophenylthiomethyl)pyrrolidine;

(3R,4S)-1-[(9-deazaadenin-9-yl)methyl]-3-hydroxy-4-(4-fluorophenylthiomethyl)pyrrolidine;

(3R,4S)-1-[(9-deazaadenin-9-yl)methyl]-3-hydroxy-4-(n-propylthiomethyl)pyrrolidine;

(3R,4S)-1-[(9-deazaadenin-9-yl)methyl]-3-hydroxy-4-(cyclohexylthiomethyl)pyrrolidine;

(3R,4S)-1-[(9-deazaadenin-9-yl)methyl]-3-hydroxy-4-(3-chlorophenylthiomethyl)pyrrolidine;

(3R,4S)-1-[(9-deazaadenin-9-yl)methyl]-3-hydroxy-4-(ethylthiomethyl)pyrrolidine;

(3R,4S)-1-[(9-deazaadenin-9-yl)methyl]-3-hydroxy-4-(phenylthiomethyl)pyrrolidine;

(3R,4S)-1-[(9-deazaadenin-9-yl)methyl]-3-hydroxy-4-(4-pyridylthiomethyl)pyrrolidine;

(3R,4S)-1-[(9-deazaadenin-9-yl)methyl]-3-hydroxy-4-n-propylpyrrolidine;

(3R,4S)-1-[(9-deazaadenin-9-yl)methyl]-3-hydroxy-4-(homocysteinylmethyl)pyrrolidine;

(3R,4S)-1-[(9-deazaadenin-9-yl)methyl]-3-hydroxy-4-(i-propylthiomethyl)pyrrolidine;

(3R,4S)-1-[(9-deazaadenin-9-yl)methyl]-3-hydroxy-4-(cyclohexylmethylthiomethyl)pyrrolidine;

(3R,4S)-1-[(9-deazaadenin-9-yl)methyl]-3-hydroxy-4-(cycloheptylthiomethyl)pyrrolidine;

(3R,4S)-1-[(9-deazaadenin-9-yl)methyl]-3-hydroxy-4-(cyclopentylthiomethyl)pyrrolidine; or (3R,4S)-1-[(9-deazaadenin-9-yl)methyl]-3-hydroxy-4-(cyclobutylthiomethyl)pyrrolidine.

14. A method as claimed in claim 1 where the cancer is prostate cancer.

15. A method as claimed in claim 1 where the cancer is head and neck cancer.

16. A method as claimed in claim 1 where the cancer is lung cancer.

\* \* \* \* \*

UNITED STATES PATENT AND TRADEMARK OFFICE
CERTIFICATE OF CORRECTION

| | | |
|---|---|---|
| PATENT NO. | : 8,916,571 B2 | Page 1 of 1 |
| APPLICATION NO. | : 12/224073 | |
| DATED | : December 23, 2014 | |
| INVENTOR(S) | : Vern L. Schramm and Chandan Guha | |

It is certified that error appears in the above-identified patent and that said Letters Patent is hereby corrected as shown below:

In the Specification

Column 1, lines 16-20, should read:

-- STATEMENT OF GOVERNMENT SUPPORT

This invention was made with government support under grant number GM041916 awarded by the National Institutes of Health. The government has certain rights in the invention. --

Signed and Sealed this
Twelfth Day of January, 2016

Michelle K. Lee
*Director of the United States Patent and Trademark Office*